United States Patent
Ikuma et al.

(10) Patent No.: US 10,433,762 B2
(45) Date of Patent: Oct. 8, 2019

(54) MEDICAL INSTRUMENT

(71) Applicant: OLYMPUS CORPORATION, Tokyo (JP)

(72) Inventors: Soichi Ikuma, Akishima (JP); Jun Hasegawa, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 867 days.

(21) Appl. No.: 14/974,424

(22) Filed: Dec. 18, 2015

(65) Prior Publication Data

US 2016/0100772 A1    Apr. 14, 2016

Related U.S. Application Data

(63) Continuation of application No. PCT/JP2014/067231, filed on Jun. 27, 2014.

(30) Foreign Application Priority Data

Jul. 2, 2013  (JP) ................................ 2013-139034

(51) Int. Cl.
A61B 5/06 (2006.01)
A61B 1/00 (2006.01)
A61B 34/20 (2016.01)

(52) U.S. Cl.
CPC ............ A61B 5/062 (2013.01); A61B 1/0002 (2013.01); A61B 1/00004 (2013.01);
(Continued)

(58) Field of Classification Search
CPC ..... A61B 5/062; A61B 5/065; A61B 1/00004; A61B 1/0002; A61B 1/00055; A61B 2034/2051
See application file for complete search history.

(56) References Cited

U.S. PATENT DOCUMENTS 5,729,129 A *  3/1998  Acker ...................... A61B 5/06
                                                    324/207.12
8,308,635 B2   11/2012  Tanaka et al.
(Continued)

FOREIGN PATENT DOCUMENTS

CN       1802119 A      7/2006
JP    2003-245242 A     9/2003
(Continued)

OTHER PUBLICATIONS

International Search Report dated Oct. 7, 2014 issued in PCT/JP2014/067231.
(Continued)

Primary Examiner — Amelie R Gillman
Assistant Examiner — Colin T. Sakamoto
(74) Attorney, Agent, or Firm — Scully, Scott, Murphy & Presser P.C.

(57) ABSTRACT

A medical instrument includes an insertion portion, first transmitting coils, second transmitting coils, a signal control unit, a position detection unit, a memory, and a position estimating unit. The signal control unit controls the first transmitting coils to transmit magnetic fields during a first predetermined period and controls the second transmitting coils to transmit magnetic fields during a second predetermined period. The position detection unit detects positions of the first transmitting coils during the first predetermined period and detects positions of the second transmitting coils during the second predetermined period. The memory stores the positions of the first transmitting coils. The position estimating unit estimates a shape of the insertion portion based on the positions of the second transmitting coils and the positions of the first transmitting coils stored in the memory.

5 Claims, 9 Drawing Sheets

(52) U.S. Cl.
CPC .......... *A61B 1/00055* (2013.01); *A61B 5/065* (2013.01); *A61B 2034/2051* (2016.02)

(56) References Cited

U.S. PATENT DOCUMENTS

| | | | | |
|---|---|---|---|---|
| 2006/0173289 A1* | 8/2006 | Aizawa | .................... | A61B 5/06 600/424 |
| 2007/0106115 A1* | 5/2007 | Sugimoto | ................ | A61B 1/31 600/117 |
| 2008/0275334 A1* | 11/2008 | Berting | .................... | A61B 5/06 600/424 |

FOREIGN PATENT DOCUMENTS

| | | | |
|---|---|---|---|
| JP | 2003-290129 A | 10/2003 | |
| JP | 2004-000551 A | 1/2004 | |
| JP | 2005-334472 A | 12/2005 | |
| JP | 2007-130174 A | 5/2007 | |

OTHER PUBLICATIONS

Japanese Office Action dated Jun. 23, 2015 issued in JP 2015-503389.
English translation of International Preliminary Report on Patentability dated Jan. 14, 2016 together with the Written Opinion received in related International Application No. PCT/JP2014/067231.
Extended Supplementary European Search Report dated Apr. 11, 2017 in European Patent Application No. 14 81 9994.6.
Chinese Office Action dated May 25, 2017 in Chinese Patent Application No. 201480037306.2.
Chinese Office Action dated Oct. 30, 2017 in Chinese Patent Application No. 201480037306.2.

* cited by examiner

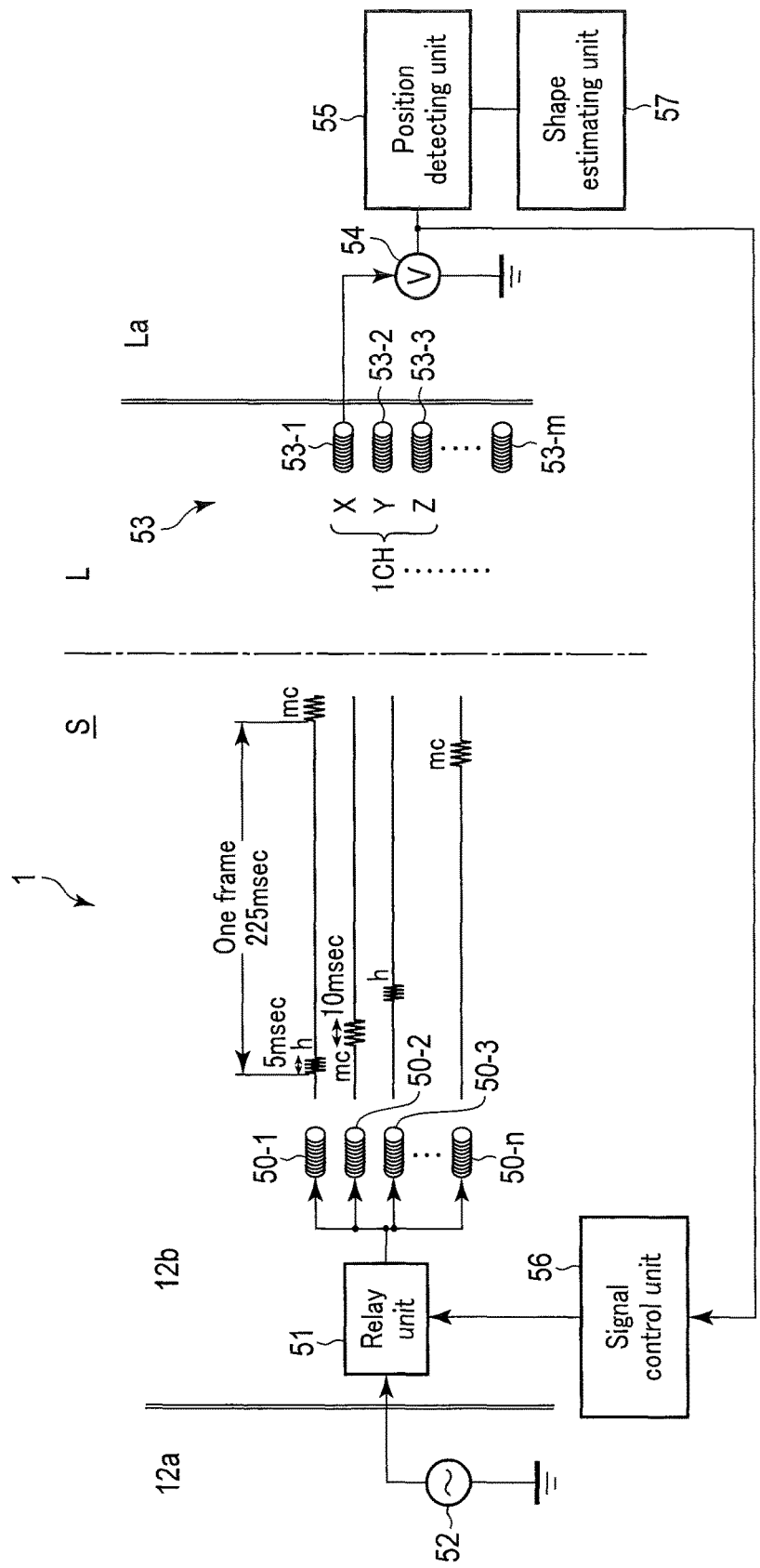
F I G. 1

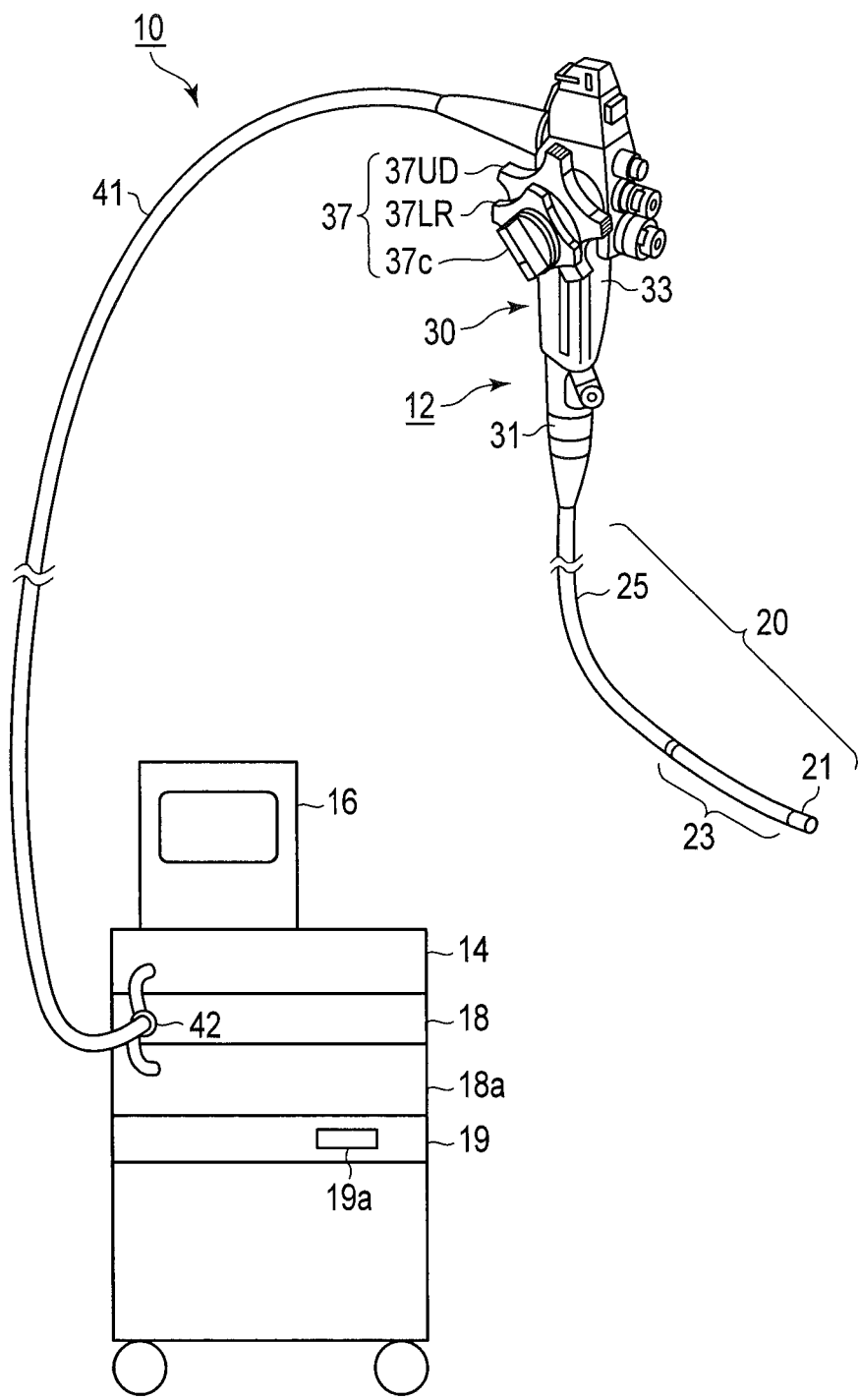
F I G. 2

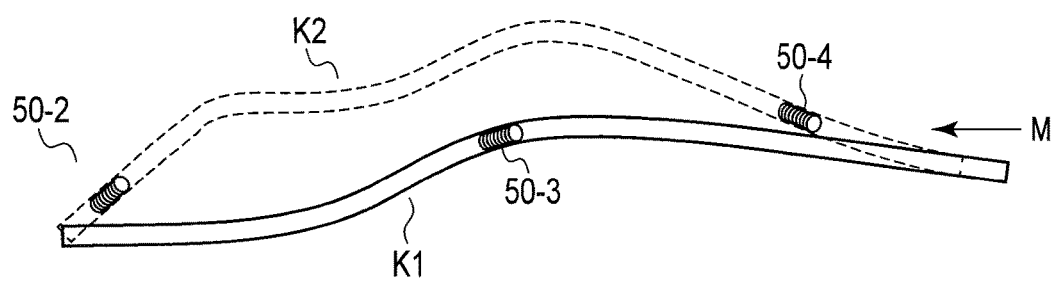
F I G. 12

MEDICAL INSTRUMENT

CROSS-REFERENCE TO RELATED APPLICATIONS

This application is a Continuation application of PCT Application No. PCT/JP2014/067231, filed Jun. 27, 2014 and based upon and claiming the benefit of priority from the prior Japanese Patent Application No. 2013-139034, filed Jul. 2, 2013, the entire contents of both of which are incorporated herein by reference.

BACKGROUND OF THE INVENTION

1. Field of the Invention

The present invention relates to a medical instrument such as an endoscope which detects, for example, a shape when the medical instrument is inserted into a subject.

2. Description of the Related Art

There is known an observation apparatus for insertion-shape of an endoscope which detects, for example, a shape when an endoscope is inserted into a subject such as a patient. This apparatus comprises a large number of transmitting coils provided in an insertion portion of the endoscope, and also comprises an antenna including a receiving coil. This apparatus transmits magnetic fields from all the transmitting coils in a time-division manner, and receives the magnetic fields by the receiving coil of the antenna, thereby detecting the positions of all the transmitting coils, and from these positions, detecting the shape of the insertion portion of the endoscope.

In Jpn. Pat. Appln. KOKAI Publication No. 2003-290129, coils C1 to C30 arranged in the insertion portion of the endoscope are classified into groups A, B, and a C, each including ten coils. The coils C1 to 010 in the group A are connected to timing circuits P1 to P10, the coils C11 to C20 in the group B are connected to timing circuits P11 to P20, and the coils C21 to C30 in the group C are connected to timing circuits P21 to P30. In Jpn. Pat. Appln. KOKAI Publication No. 2003-290129, the timing circuits P1 to P30 are connected to 10 oscillators which have different oscillating frequencies. In such a configuration, according to Jpn. Pat. Appln. KOKAI Publication No. 2003-290129, each of ten timing circuits, for example, each of the timing circuits P1 to P10, P11 to P20, and P21 to P30, ... is intermittently turned on by coil driving timing signals INTMT01 to 30 from a control circuit 51. Thus, Jpn. Pat. Appln. KOKAI Publication No. 2003-290129 discloses that each of the coils C1 to 010, C11 to C20, and C21 to C30 belonging to each of the groups A, B, and C is sequentially and intermittently driven, so that it is possible to handle cases in which the number of coils is large.

In Jpn. Pat. Appln. KOKAI Publication No. 2003-245242, a midpoint dPmi of an arc is found by interpolation processing of detection points Pi and Pi+1 of source coils arranged in the insertion portion. When the length of the arc is substantially equal to the actual arrangement interval of the source coils, the midpoint dPmi is set as an ideal point. When the length of the arc is much smaller than the actual arrangement interval of the source coils, a point Pvi extending from a midpoint of line segments Pi and Pi+1 in a direction to connect the midpoint dPmi of the arc is set as an ideal point, and the line segments Pi and Pi+1 including the ideal point Pvi are subjected to interpolation processing. Thus, Jpn. Pat. Appln. KOKAI Publication No. 2003-245242 discloses that the shape of the insertion portion can be accurately detected as if a source coil is disposed at the ideal point.

BRIEF SUMMARY OF THE INVENTION

A medical instrument according to an aspect of the invention is a medical instrument comprising: a medical instrument comprising: an insertion portion to be inserted into a subject; first transmitting coils provided in the insertion portion along a longitudinal direction of the insertion portion at predetermined intervals and generating magnetic fields; second transmitting coils provided at positions different from positions of the first transmitting coils in the insertion portion along the longitudinal direction of the insertion portion at predetermined intervals and generating magnetic fields; a signal control unit which controls the first transmitting coils to transmit the magnetic fields during a first predetermined period and controls the second transmitting coils to transmit the magnetic fields during a second predetermined period different from the first predetermined period; a position detection unit which detects positions of the first transmitting coils on the basis of the magnetic field during the first predetermined period and detects positions of the second transmitting coils on the basis of the magnetic field during the second predetermined period; a memory which stores the positions of the first transmitting coils detected by the position detection unit during the first predetermined period; and a position estimating unit which estimates a shape of the insertion portion on the basis of the positions of the second transmitting coils detected by the position detection unit during the second predetermined period and the positions of the first transmitting coils stored in the memory.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a configuration diagram showing an embodiment of a medical instrument according to the present invention;

FIG. 2 is a configuration diagram showing an endoscope apparatus to which the same instrument is applied;

FIG. 12 is a diagram showing one example of the actual shape of the insertion portion and the actual position of each transmitting coil provided therein in the first frame and the second frame in the same instrument;

DETAILED DESCRIPTION OF THE INVENTION

First Embodiment

Figure 3:
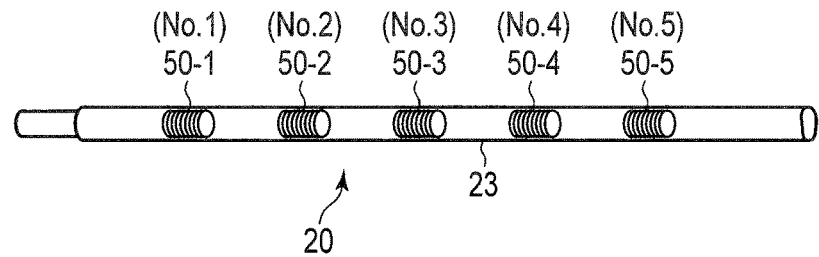
FIG. 3 is a diagram showing an insertion portion of the same instrument in which several transmitting coils are provided.

Hereinafter, a first embodiment of the present invention will be described with reference to the drawings.

FIG. 1 shows a configuration diagram of a medical instrument (hereinafter referred to as the instrument) 1. The instrument 1 is provided in, for example, an endoscope apparatus (tubular insertion system) 10 shown in FIG. 2. The endoscope apparatus 10 includes an insertion portion 20 to be inserted into a body cavity (lumen) of, for example, a patient who is a subject. The endoscope apparatus 10 inserts the insertion portion 20 into, for example, a body cavity to observe and treat an affected part or a lesioned part in the body cavity.

The present instrument 1 detects the position of the insertion portion 20 or a shape such as a looped shape when the insertion portion 20 is inserted in the body cavity of the patient. The instrument 1 is applicable to the detection of the position and shape of not only the endoscope apparatus 10 but also, for example, a forceps or a catheter used in the endoscope apparatus 10.

The endoscope apparatus 10 includes an endoscope 12, an image processor 14 such as a video processor, a monitor 16, a light source 18, an insertion shape estimating device 18a, and a controller 19. The endoscope 12 images the inside of the body cavity of, for example, the patient as shown in FIG. 2. The image processor 14 processes the image of the inside of the body cavity of, for example, the patient taken by the endoscope 12. The monitor 16 displays the image of the inside of the body cavity of, for example, the patient processed by the image processor 14.

The light source 18 emits illumination light which is output from the endoscope 12 to illuminate the inside of the body cavity of, for example, the patient. The insertion shape estimating device 18a supplies electric power to transmitting coils as multiple elements such as transmitting coils 50-1 to 50-$n$ ($n$: natural number), and detects the voltages of receiving coils in an antenna as multiple elements such as receiving coils 53-1 to 53-$m$ ($m$: natural number) that is included in an antenna 53 and estimates an insertion shape. The controller 19 respectively controls the endoscope 12, the image processor 14, the monitor 16, the light source 18, and the insertion shape estimating device 18a to control the operation of the whole endoscope apparatus 10 for observing and treating an affected part or a lesioned part in the body cavity of, for example, the patient.

Specific explanations are given below. The endoscope 12 is intended to observe and treat the body cavity of, for example, the patient. The insertion portion 20 and an operation unit are provided with the endoscope 12. The operation unit 30 is coupled to the proximal end of the insertion portion 20 and serves to operate the endoscope 12. The insertion portion 20 is formed into a hollow and elongated tubular shape.

The insertion portion 20 includes a distal rigid portion 21, a curving portion 23, and a flexible tubular portion 25. The distal rigid portion 21, the curving portion 23, and the flexible tubular portion 25 are continuously formed from the distal end of the insertion portion 20 toward the proximal end. The distal rigid portion 21 is made of a rigid material. The proximal end of the distal rigid portion 21 is coupled to the distal end of the curving portion 23. The distal rigid portion 21 is the distal end of the insertion portion 20, i.e., the distal end of the endoscope 12.

The curving portion 23 curves in a direction desired by an operator in UDLR directions in response to an operational instruction issued by the operator to a curving operation portion 37. The curving portion 23 is formed to be curvable in, for example, upward, downward, leftward, and rightward (UDLR) directions. The proximal end of the curving portion 23 is coupled to the proximal end of the flexible tubular portion 25. The position and direction of the distal rigid portion 21 change in accordance with the curving of the curving portion 23. As a result, an image in which the inside of the body cavity of, for example, the patient is caught from a given direction can be brought into an observation field of the endoscope 12. The illumination light output from the endoscope 12 is applied to the inside of the body cavity (lumen) of, for example, the patient. Joint rings of the curving portion 23 are rotatably joined along the longitudinal axis direction of the insertion portion 20.

The flexible tubular portion 25 is a tubular member extending from a body 31 of the operation unit 30. The flexible tubular portion 25 is made of a flexible member, and curves by receiving external force.

The operation unit 30 is grasped by the operator, and operated to curve the insertion portion 20 in the upward, downward, leftward, and rightward (UDLR) directions. The operation unit 30 includes the body 31 which extends the flexible tubular portion 25, a handle 33 which is coupled to the proximal end of the body 31 and which is held by the operator who operates the endoscope 12, and a universal cord 41 connected to the handle 33.

The curving operation portion 37 for curving the curving portion 23 is provided in the handle 33. For example, an operation wire is extended between the curving operation portion 37 and the curving portion 23. The curving operation portion 37 curves the curving portion 23 upward and downward (UD) and leftward and rightward (LR) by moving the operation wire in the axial direction of this operation wire between the operation wire and the curving portion 23. The curving operation portion 37 includes an upward/downward curving operation knob 37UD for curving the curving portion 23 upward/downward (UD), a leftward/rightward operation knob 37LR for curving the curving portion 23 leftward/rightward (LR), and a fixing knob 37c which fixes the position of the curved curving portion 23.

The universal cord 41 electrically connects the handle 33, the image processor 14, the light source 18, and the insertion shape estimating device 18a to perform data communication. One end of the universal cord 41 extends from the side surface of the handle 33. A connector 42 is provided at the other end of the universal cord 41. The connector 42 can be connected to and disconnected from the image processor 14, the light source device 18, and the insertion shape estimating device 18a, respectively.

The transmitting coils 50-1 to 50-n, for example, 30 transmitting coils 50-1 to 50-n (n=30) are provided in the insertion portion 20 along the longitudinal direction at predetermined intervals. FIG. 3 shows the curving portion 23 of the insertion portion 20 in which five transmitting coils 50-1 to 50-5 among the 30 transmitting coils provided in the insertion portion 20 are provided.

The transmitting coils 50-1 to 50-n generate alternating magnetic fields (hereinafter abbreviated as magnetic fields) by receiving electric power supply, and transmit these magnetic fields. The respective transmitting coils 50-1 to 50-n are provided, for example, from the distal end of the insertion portion 20 in the order of the No. 1 transmitting coil 50-1, the No. 2 transmitting coil 50-2, . . . , and the No. n transmitting coil 50-n.

Each of the transmitting coils 50-1 to 50-n is connected to a transmission electric power supply 52 via a relay unit 51 for selectively supplying electric power to each of the transmitting coils 50-1 to 50-n as shown in FIG. 1. The relay unit 51 is provided in, for example, the connector 42 or the operation unit 30. The relay unit 51 comprises relays that are respectively connected to, for example, the transmitting coils 50-1 to 50-n. The relay unit 51 turns on the relay corresponding to, for example, the transmitting coil 50-1 which transmits a magnetic field among the relays so that alternating electric power is supplied to the transmitting coil 50-1 from the transmission electric power supply 52 via the relay.

The transmission electric power supply 52 is provided in the insertion shape estimating device 18a. The transmission electric power supply 52 outputs the alternating electric power having a predetermined frequency. The transmission electric power supply 52 supplies electric power to each of the transmitting coils 50-1 to 50-n via the relay unit 51. The electric power is supplied via electric power supply lines provided in, for example, the universal cord 41. A transmission unit includes, for example, each of the transmitting coils 50-1 to 50-n, the relay unit 51, and the transmission electric power supply 52.

The receiving coils 53-1 to 53-m included in the antenna 53, for example, 12 (m=12) receiving coils are provided. Each of the receiving coils 53-1 to 53-m detects each of the magnetic fields transmitted from each of the transmitting coils 50-1 to 50-n. Each of the receiving coils 53-1 to 53-m is provided in an examination room or an operation room for, for example, observing and treating the inside of the body cavity of a subject such as a patient, outside the patient. When the inside of the body cavity of the patient lying in bed is observed and treated, each of the receiving coils 53-1 to 53-m is provided within a range in which each of the receiving coils 53-1 to 53-m can detect each of the magnetic fields transmitted from each of the transmitting coils 50-1 to 50-n of the insertion portion 20 inserted in the body cavity of, for example, the patient.

There are a total of 12 receiving coils among the receiving coils 53-1 to 53-m: for example, four receiving coils having axes arranged in an x-direction, four receiving coils having axes arranged in a y-direction, and four receiving coils having axes arranged in a z-direction. Each of the receiving coils 53-1 to 53-m is disposed at a different position in the area in which the magnetic field can be detected by the antenna 53. The receiving coils 53-1 to 53-m respectively detect the magnetic fields transmitted from the transmitting coils 50-1 to 50-n in the xyz directions, and generate voltages corresponding to the magnitude of the magnetic fields in the xyz directions at both ends of the receiving coils 53-1 to 53-m.

Voltage detectors 54 are respectively connected to the output terminals of the receiving coils 53-1 to 53-m. Each of the voltage detectors 54 is provided in the insertion shape estimating device 18a. Each of the voltage detectors 54 detects the level of each of the voltages generated at the output terminal of each of the receiving coils 53-1 to 53-m, and outputs each voltage detection signal corresponding to each of the voltage levels. Each of the voltage detection signals is sent to a position detection unit 55 provided in the insertion shape estimating device 18a.

Each of the voltage detection signals output from the voltage detectors 54 is input to the position detection unit 55. The position detection unit 55 detects the coil position and coil direction of each of the transmitting coils 50-1 to 50-n on the basis of the magnitude of each of the voltage levels indicated by each of the voltage detection signals, that is, the magnitude of each of the magnetic fields in the xyz directions. Each of the coil positions and directions of the transmitting coils 50-1 to 50-n is stored in a memory 19a as positional information. A receiving unit includes, for example, each of the receiving coils 53-1 to 53-m, the voltage detector 54, and the position detection unit 55.

A signal control unit 56 is provided in the insertion shape estimating device 18a. The signal control unit 56 sequentially drives to turn on and off the relays of the relay unit 51. As a result of this on/off driving, electric power is sequentially supplied to the transmitting coils 50-1 to 50-n from the transmission electric power supply 52 through the relays of the relay unit 51. Thus, the magnetic fields are sequentially transmitted from the transmitting coils 50-1 to 50-n in a time-division manner. In this case, magnetic fields are sequentially transmitted to the receiving coils 53-1 to 53-m from the transmitting coils 50-1 to 50-n.

A period up to the end of the transmission of the magnetic fields from all the transmitting coils 50-1 to 50-n is one frame period. The signal control unit 56 performs, for multiple frame periods in succession, the operation of the one frame period for sequentially transmitting the magnetic fields from all the transmitting coils 50-1 to 50-n.

The signal control unit 56 controls predetermined transmitting coils among the transmitting coils 50-1 to 50-n to transmit magnetic fields in a time-division manner. The predetermined transmitting coils are, for example, even-numbered (first position) transmitting coils from the distal end of the insertion portion 20 among the transmitting coils 50-1 to **50-*n*, that is, the No. 2 transmitting coil 50-2, the No. 4 transmitting coil 50-4, . . . , and the No. n transmitting coil 50-*n* (n=30); and odd-numbered (second position) transmitting coils from the distal end of the insertion portion 20, that is, the No. 1 transmitting coil 50-1, the No. 3 transmitting coil 50-3, . . . , and the No. n−1 transmitting coil 50-*n*** (n=30).

Therefore, the signal control unit 56 sequentially controls, for example, the even-numbered transmitting coils 50-2, 50-4, . . . , and **50-*n*** (n=30) one by one to transmit a magnetic field in a time-division manner.

The signal control unit 56 sequentially controls, for example, the odd-numbered transmitting coils 50-1, 50-3, . . . , and **50-*n*** (n=30) one by one to transmit a magnetic field in a time-division manner.

To avoid complicated descriptions, the transmitting coils 50-1 to **50-*n* are abbreviated as the even-numbered transmitting coils 50-2, . . . , and 50-*n* and as the odd-numbered transmitting coils 50-1, . . . , and 50-*n*−1**.

Specifically, the signal control unit 56 sequentially controls all the transmitting coils 50-1 to **50-*n*** to transmit magnetic fields in a time-division manner in an initial frame period (first) among multiple frame periods.

The signal control unit 56 sequentially controls the even-numbered transmitting coils 50-2, . . . , and **50-*n*** one by one to transmit a magnetic field in a time-division manner in a predetermined first frame period, for example, the even-numbered frame period among the successive frame periods (second and subsequent frame periods) after the initial frame period.

The signal control unit 56 sequentially controls the odd-numbered transmitting coils 50-1, . . . , and **50-*n*−1** one by one to transmit a magnetic field in a time-division manner in a second frame period, for example, the odd-numbered frame period which is a frame period after a predetermined frame period among the frame periods (second and subsequent frame periods).

A shape estimating unit 57 is provided in the insertion shape estimating device 18*a*. The shape estimating unit 57 estimates the coil positions (the odd-numbered transmitting coils 50-1, . . . , and **50-*n*−1 or the even-numbered transmitting coils 50-2, . . . , and 50-*n*) other than the predetermined coils (the even-numbered transmitting coils 50-2, . . . , and 50-*n* or the odd-numbered transmitting coils 50-1, . . . , and 50-*n*−1) on the basis of the positional information comprising the coil positions and coil directions of the transmitting coils 50-1 to 50-*n***.

The shape estimating unit 57 estimates the shape, for example, looped shape of the insertion portion 20 on the basis of the estimated coil positions and coil directions of the coils (the odd-numbered transmitting coils 50-1, . . . , and **50-*n*−1 or the even-numbered transmitting coils 50-2, . . . , and 50-*n*), the coil positions and coil directions of the predetermined coils (the even-numbered transmitting coils 50-2, . . . , and 50-*n* or the odd-numbered transmitting coils 50-1, . . . , and 50-*n*−1) detected by the signal control unit 56 when the magnetic fields are transmitted from the predetermined coils, and each of distances between the transmitting coils 50-1 to 50-*n* (which is a distance along a scope shape and which is a value, e.g., 100 mm known from a design value of a scope). Here, the scope corresponds to the insertion portion 20 of the endoscope apparatus 10**.

In the initial frame period, when the magnetic fields are sequentially transmitted from the transmitting coils 50-1 to **50-*n* in a time-division manner, the shape estimating unit 57 estimates the shape, for example, looped shape of the insertion portion 20 by linking the coil positions of the transmitting coils 50-1 to 50-*n* on the basis of the coil positions and coil directions of the transmitting coils 50-1 to 50-*n* detected by the position detection unit 55, and each of the distances between the transmitting coils 50-1 to 50-*n*** (e.g., 100 mm).

In each of the frame periods after the initial frame period, the shape estimating unit 57 estimates the shape, for example, looped shape of the insertion portion 20 by linking the coil positions of the transmitting coils 50-1 to **50-*n* on the basis of the estimated coil positions, that is, the coil positions of the even-numbered transmitting coils 50-2, . . . , and 50-*n*, the positions and magnetic field directions of the predetermined coils already detected by the position detection unit 55 in a frame period closest to (e.g., a frame period which is one frame period before) the current frame period, and each of the distances between the transmitting coils 50-1 to 50-*n* (e.g., 100 mm). The positions of the predetermined coils already detected in the frame period closest to the current frame period are, for example, the coil positions of the odd-numbered transmitting coils 50-1, . . . , and 50-*n*−1**.

In each of the frame periods after the initial frame period, the shape estimating unit 57 estimates the shape, for example, looped shape of the insertion portion 20 by linking the coil positions of the transmitting coils 50-1 to **50-*n* on the basis of the estimated coil positions, that is, the coil positions of the odd-numbered transmitting coils 50-1, . . . , and 50-*n*−1, the positions of the predetermined coils already detected by the position detection unit 55 in a frame period closest to the current frame period, for example, a frame period which is one frame period before the current frame period, for example, the coil positions and coil directions of the even-numbered transmitting coils 50-2, . . . , and 50-*n*, and each of the distances between the transmitting coils 50-1 to 50-*n*** (e.g., 100 mm).

The associated operations of the signal control unit 56 and the shape estimating unit 57 are specifically described.

In each of the first frame periods, for example, the even-numbered frame periods among the successive frame periods after the initial frame period, the signal control unit 56 sequentially controls the even-numbered transmitting coils 50-2, . . . , and **50-*n* among all the transmitting coils 50-1 to 50-*n*** to transmit magnetic fields in a time-division manner.

In addition, in each of the even-numbered frame periods, the shape estimating unit 57 estimates the shape, for example, looped shape of the insertion portion 20 by linking the coil positions of the transmitting coils 50-1 to **50-*n* on the basis of the coil positions and coil directions of the even-numbered transmitting coils 50-2, . . . , and 50-*n* detected by the position detection unit 55 when the magnetic fields are transmitted from the even-numbered transmitting coils 50-2, . . . , and 50-*n* in a time-division manner, the coil positions and coil directions of the transmitting coils other than the even-numbered transmitting coils 50-2, . . . , and 50-*n* already detected by the position detection unit 55 in a frame period closest to each of this even-numbered frame periods, for example, in a previous frame period, that is, the odd-numbered transmitting coils 50-1, . . . , and 50-*n*−1, and each of the distances between the transmitting coils 50-1 to 50-*n***.

Figure 4:
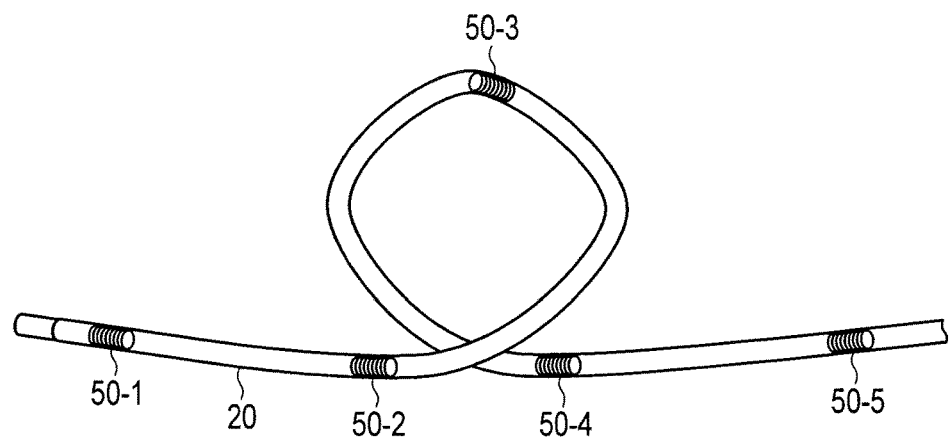
FIG. 4 is a diagram showing the estimation of the position of the insertion portion of the same instrument and a shape such as a looped shape.

For example, in each of the even-numbered frame periods, each of the coil positions of the even-numbered transmitting coils 50-2, 50-4, and others is detected by the position detection unit 55 as shown in FIG. 4 when the magnetic fields are sequentially transmitted from the even-numbered transmitting coils 50-2, 50-4, and others in a time-division manner.

In the same frame period, the coil positions already detected by the position detection unit 55 in the recent frame period, for example, in the previous frame period and then stored in the memory 19a are used as the coil positions of the odd-numbered transmitting coils 50-1, 50-3, and others which have not been detected by the position detection unit 55.

Therefore, the shape estimating unit 57 estimates the shape, for example, looped shape of the insertion portion 20 on the basis of each of the coil positions of the even-numbered transmitting coils 50-2, 50-4, and others, each of the coil positions of the odd-numbered transmitting coils 50-1, 50-3, and others which have been already detected by the position detection unit 55 and then stored in the memory 19a, and each of the distances between the transmitting coils 50-1 to 50-n.

On the other hand, in the second frame period, for example, the odd-numbered frame period among the frame periods after the initial frame period, the signal control unit 56 sequentially controls the odd-numbered transmitting coils 50-1, . . . , and 50-n−1 among all the transmitting coils 50-1 to 50-n to transmit magnetic fields in a time-division manner.

In addition, in each of the odd-numbered frame periods, the shape estimating unit 57 finds each of the coil positions of all the transmitting coils 50-1 to 50-n on the basis of each of the coil positions of the odd-numbered transmitting coils 50-1, . . . , and 50-n−1 detected by the position detection unit 55 when the magnetic fields are transmitted from the odd-numbered transmitting coils 50-1, . . . , and 50-n−1 in a time-division manner, and the coil positions and coil directions of the even-numbered transmitting coils 50-2, . . . , and 50-n already detected by the position detection unit 55 and then stored in the memory 19a in a frame period closest to each of this odd-numbered frame periods, for example, in a previous frame period. The shape estimating unit 57 estimates the shape, for example, looped shape of the insertion portion 20 on the basis of each of the coil positions of all the transmitting coils 50-1 to 50-n, the direction of each of the coils 50-1 to 50-n, and each of the distances between the transmitting coils 50-1 to 50-n.

The position of the insertion portion 20 and a shape such as a looped shape are estimated by the shape estimating unit 57 based on the following assumed conditions of the endoscope 12. The first condition is that the insertion portion 20 of the endoscope 12 does not extend or contract. The second condition is that there is a limit to how the endoscope 12 curves.

Each of the spaces between the transmitting coils 50-1 to 50-n does not change because the insertion portion 20 does not extend or contract. Each of the spaces between the transmitting coils 50-1 to 50-n is a distance along the scope shape, and is known from a design value of the scope. The endoscope 12 has a limit in the way of curving; for example, the endoscope 12 cannot rapidly be bent in a curvature radius R 30 mm or less. A circumference at a curvature radius R of 30 mm is about 188 mm. Therefore, if each of the distances between the transmitting coils 50-1 to 50-n is 100 mm, at least one transmitting coil exists in the loop formed by the insertion portion 20. As a result, even the position of the insertion portion 20 having the loop is identified.

In the present embodiment, in the even- or odd-numbered frame period, the magnetic fields are sequentially transmitted from the even- or odd-numbered transmitting coils in a time-division manner, and each of the coil positions of the even- or odd-numbered transmitting coils is detected. The undetected coil positions of the even- or odd-numbered transmitting coils are detected by use of each of the coil positions of the even- or odd-numbered transmitting coils that have been already detected in the closest frame period. The positions of all the transmitting coils are linked to estimate the position of the insertion portion 20 and a shape such as a looped shape.

[Inter-Transmission-Coil Shape Estimation Method]

A method of shape estimation between two transmitting coils in the transmitting coils 50-1 to 50-n is specifically described below with reference to FIG. 5 to FIG. 10.

Figure 5:
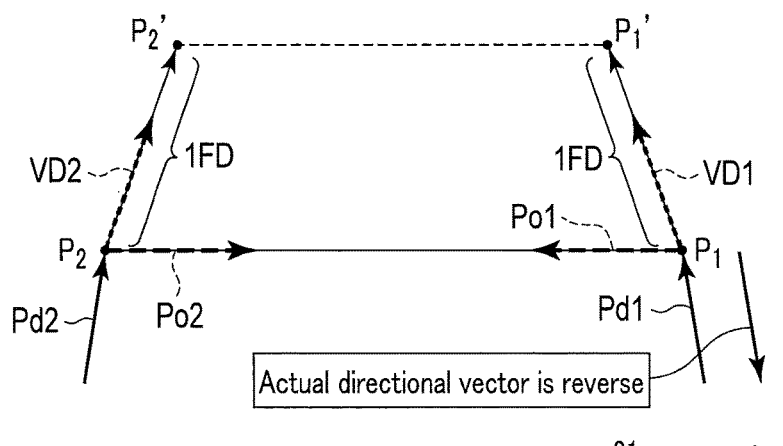
FIG. 5 is a diagram showing terms and abbreviations used in the explanation of a method of shape estimation between two coils in the same instrument.

The shapes of the parts between the transmitting coils 50-1 to 50-n are estimated by sequentially finding pairs of interpolation points from two interpolation target transmitting coils, for example, the transmitting coils 50-1 and 50-2, and linking all these interpolation points. Terms and abbreviations used in the explanation of the method of shape estimation between two coils are as follows, and some of them are shown in FIG. 5.

The front (coil) is the coil (the transmitting coil 50-1) on the distal side of the endoscope 12 of the two interpolation target coils (e.g., the transmitting coils 50-1 and 50-2). The coordinates of the front coil are P1. The reference sign 21a indicates the distal direction of the insertion portion 20.

The rear (coil) is the coil (the transmitting coil 50-2) on the proximal side of the endoscope 12 of the interpolation target coils (e.g., the transmitting coils 50-1 and 50-2). The coordinates of the rear coil are P2.

The number of interpolations is a number to which 1 is added to the number of interpolation points.

One interpolation distance (1FD) is a value obtained by dividing the distance between the interpolation target coils (e.g., the transmitting coils 50-1 and 50-2) by the number of interpolations. For example, when the distance is 100 mm and the number of interpolations is 10, one interpolation distance is 10 mm.

A current point is an interpolation point determined at the time of the determination of the previous interpolation point. The first interpolation point determination current point is a point indicating each of the two interpolation target coils.

Current directional vectors Pd1 and Pd2 are interpolation orbit directional vectors VD1 and VD2 determined at the time of the determination of the previous interpolation point. The current directional vectors used at the time of the determination of the first interpolation point are directional vectors indicating each of the two interpolation target coils.

The interpolation orbit directional vectors VD1 and VD2 are unit directional vectors which have been corrected by an interpolation ratio to determine the coordinates of the next interpolation point. For the interpolation ratio, refer to the setting of one interpolation ratio, which will be described later, and the interpolation orbital directions VD1 and VD2.

Object directional vectors Po1 and Po2 are unit directional vectors facing toward the interpolation points to pair with, on the side of the other coil side from the current points. The object directional vector used at the time of the determination of the first interpolation point is a unit directional vector facing from the coordinates indicating one interpolation target coil toward the coordinates indicating another interpolation target coil.

The interpolation points are points located at the coordinates which have moved one interpolation distance from the current points toward the interpolation orbital directions VD1 and VD2. The number of interpolation points existing between the interpolation target coils is the number of interpolations−1.

During interpolation processing, the inverted vector of the actual directional vector is treated as the directional vector of the front coil.

[Setting of Interpolation Ratio and Interpolation Orbital Directions]

The basic ratio to find the interpolation ratio is defined as follows.

The basic ratio starts from (1−(1/number of interpolations)), and is a value which decreases by (2/number of interpolations) whenever a pair of front and rear interpolation points are determined.

Two points are determined in one interpolation process, so that, for example, when the number of interpolations is N, the basic ratio is $$(1-1/N) \rightarrow (1-3/N) \rightarrow (1-5/N) \rightarrow (1-7/N).$$

The value obtained by multiplying the length of a line segment connecting the end points of the current directional vectors Pd1 and Pd2 and the endpoints of the object directional vectors Po1 and Po2 by the basic ratio is an interpolation ratio 1. The value of the length of a line segment connecting the end points of the current directional vectors Pd1 and Pd2 and the end points of the object directional vectors Po1 and Po2 is an interpolation ratio 2.

(a) Case in which Interpolation Ratio 2≥Interpolation Ratio 1 is Satisfied m(interpolation ratio 1), n(interpolation ratio 2−interpolation ratio 1). Unit vectors of vectors in which the current points are starting points and in which points that internally divide line segments connecting the end points of the current directional vectors Pd1 and Pd2 and the end points of the object directional vectors Po1 and Po2 by m:n from the side of the end points of the object directional vectors Po1 and Po2 are endpoints are the interpolation orbital direction vectors VD1 and VD2.

(b) Case in which Interpolation Ratio 2<Interpolation Ratio 1 is Satisfied n(interpolation ratio 1), m(interpolation ratio 1−interpolation ratio 2). Unit vectors of vectors in which the current points are starting points and in which points that externally divide line segments connecting the end points of the current directional vectors Pd1 and Pd2 and the end points of the object directional vectors Po1 and Po2 by n:m from the side of the end point of the object directional vector Po are end points are the interpolation orbital direction vectors VD1 and VD2.

The interpolation ratio and the interpolation orbital direction VD to determine the first interpolation point and the second interpolation point are as follows. The third and subsequent points are found in a manner similar to the second point, and are therefore omitted.

Here, N is the number of interpolations.

Figure 6:
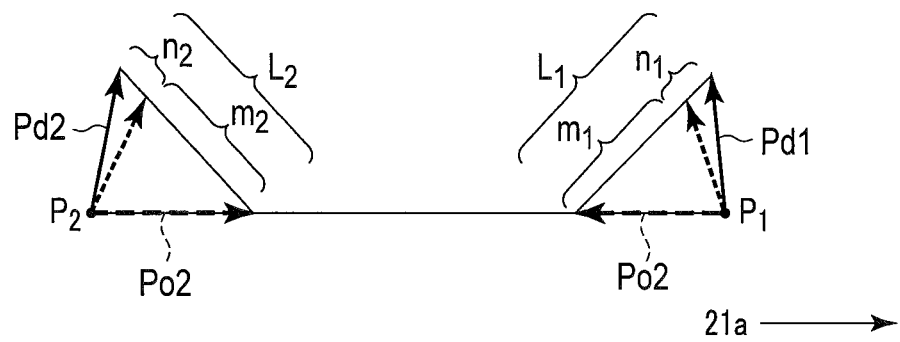
FIG. 6 is a diagram illustrating the method of shape estimation between two coils in the determination of the first interpolation point in the same instrument.

$L_1$ is the length (front) of a line segment which connects the end point of the current directional vector Pd1 started from the coil position of the distal side coil (the transmitting coil 50-1) and the end point of the object directional vector Po1 as shown in FIG. 6.

$L_2$ is the length (rear) of a line segment which connects the end point of the current directional vector Pd2 started from the coil position of the proximal side coil (the transmitting coil 50-2) and the end point of the object directional vector Po2.

(At the Time of the Determination of the First Interpolation Point)

An explanation is given with reference to FIG. 6. An internally dividing point is used because interpolation ratio 2≥interpolation ratio 1 is always satisfied.

$L_1 \times (1-1/N), L_2 \times (1-1/N)$      Interpolation ratio 1

$L_1, L_2$      Interpolation ratio 2

$m_1 : L_1 \times (1-1/N)$ $m_2 : L_2 \times (1-1/N)$ $n1 : L_1 \times N$ $n_2 : L_2 \times N$ Unit vectors of the vectors indicated by dotted arrows are the interpolation orbital direction vectors VD1 and VD2.

Figure 7:
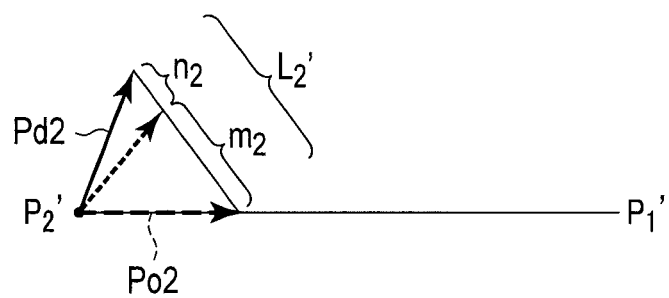
FIG. 7 is a diagram illustrating the method of shape estimation between two coils in the determination of the second interpolation point in the same instrument.

FIG. 7 shows the rear coil by way of example, and the same method is also applied to the front coil.

(At the Time of the Determination of the Second Interpolation Point)

$L_1 \times (1-3/N), L_2 \times (1-3/N)$      Interpolation ratio 1

$L_1', L_2'$      Interpolation ratio 2

(for $L_2'$, see FIG. 7. $L_2'$ corresponds to $L_2$ in the case of the second point)

(i) Case in which Interpolation Ratio 2 Interpolation Ratio 1 is Satisfied $m_1 : L_1 \times (1-1/N)$ $m_2 : L_2 \times (1-1/N)$ $n1 : L_1' - (L_1 \times (1-3/N))$ $n_2 : L_2' - (L_2 \times (1-3/N))$ (ii) Case in which Interpolation Ratio 2<Interpolation Ratio 1 is Satisfied $L_1 \times (1-3/N), L_2 \times (1-3/N)$      Interpolation ratio 1

$L_1', L_2'$      Interpolation ratio 2

Figure 8:
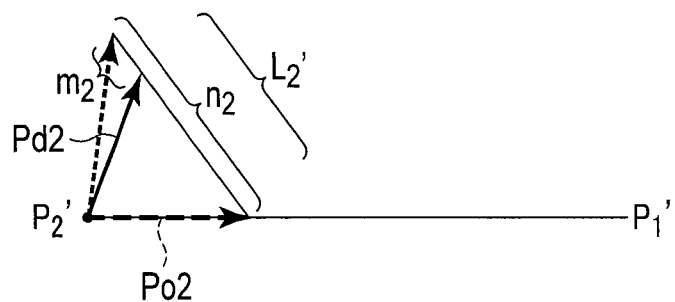
FIG. 8 is a diagram illustrating an interpolation ratio in the determination of the second interpolation point in the same instrument.

(for $L_2'$, see FIG. 8. $L_2'$ corresponds to $L_2$ in the case of the second point)

$m_1 : (L_1 \times (1-3/N)) - L_1'$ $m_2 : (L_2 \times (1-3/N)) - L_2'$ $n1 : L_1 \times (1-3/N))$ $n_2 : L_2 \times N(1-3/N)$ Unit vectors of the vectors indicated by dotted arrows are the interpolation orbital direction vectors VD1 and VD2.

[Determination of Interpolation Points]

Figure 9:
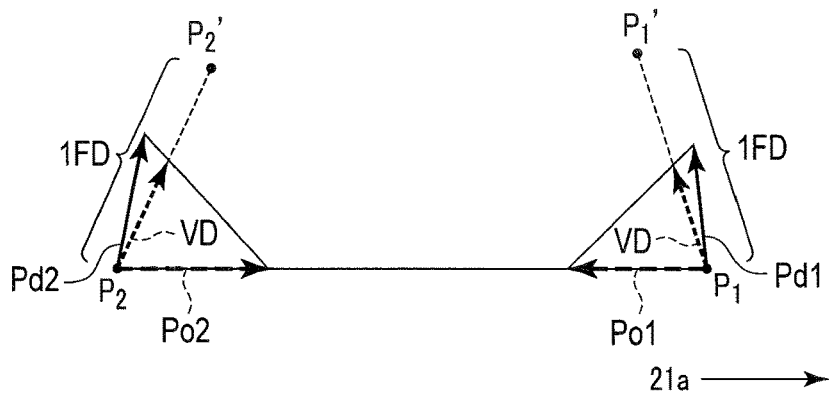
FIG. 9 is a diagram illustrating the setting of interpolation points in the determination of the second interpolation point in the same instrument.

Points of coordinates which have moved one interpolation distance from the current points toward the interpolation orbital direction vectors VD1 and VD2 found in the previous chapter are next interpolation points, for example, $P_1'$ and $P_2'$ shown in FIG. 9.

These interpolation points $P_1'$ and $P_2'$ are found by moving one interpolation distance from the current points in a straight line. However, when the actual shape of the insertion portion is taken into account, it is considered that a smooth movement distance corresponding to a circular arc should be the one interpolation distance. Thus, the interpolation points that have been found, the current points, and the previous interpolation point are used to reset interpolation points.

At the time of the determination of the first interpolation point, the current point is the coil position, and the previous interpolation point is the position which has moved one interpolation distance from the point of the coil position in a direction opposite to the current directional vector. At the time of the second point, the previous interpolation point is the point of the coil position.

Figure 10:
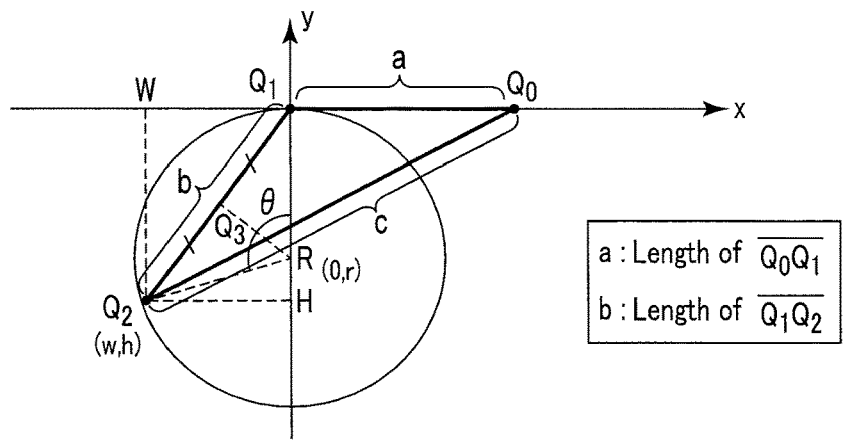
FIG. 10 is a diagram illustrating the setting of interpolation points in the determination of the second interpolation point in the same instrument.

FIG. 10 can be drawn when $Q_0$ is the previous interpolation point, $Q_1$ is the current point, $Q_2$ is the interpolation point that has been found, and $Q_3$ is the midpoint between the current point $Q_1$ and the interpolation point $Q_2$.

A sphere is desirable if a three-dimensional coordinate system is considered. However, it is assumed here that three points are on a two-dimensional coordinate system, and an auxiliary circle is created, and then an interpolation point is reset so that the circular arc of the auxiliary circle will be the one interpolation distance.

(a) An area S of $\Delta Q_0 Q_1 Q_2$ is found by use of Heron's formula.

When $s=(a+b+c)/2$, the area S of $\Delta Q_0 Q_1 Q_2$ can be found by

[Expression 1]

$$S=\sqrt{s \times (s-a) \times (s-b) \times (s-c)} \quad (1)$$

(b) Coordinates (w, h) of $Q_2$ existing in the third quadrant when $Q_1$ is assumed to be an origin are the following values.

$$S=a \times (-h)/2$$

$$\therefore h=-2 \times S/a$$

$\Delta Q_1 Q_2 W$ is a right triangle. Therefore, w is as follows:

[Expression 2]

$$\therefore w=-\sqrt{b^2-h^2} \quad (2)$$

(c) A central point R(0, r) of a circle passing through $Q_1$ and $Q_2$ is found.

A linear equation with two unknowns that represents a straight line passing through a line segment $Q_1$-$Q_2$ is represented by $$y=a_1 \times x$$

when the inclination is $a_1(=-h/w)$.

$\Delta Q_1 Q_2 W$ is an isosceles triangle, so that the central point R exists on a straight line which passes through a midpoint $Q_3(w/2, h/2)$ of the line segment $Q_1$-$Q_2$ and which intersects at right angles with this line segment $Q_1$-$Q_2$.

If the inclination of this straight line is $a_2$, a linear equation with two unknowns that represents this straight line is represented by $$y=a_2 \times x+r.$$

$$a_2=-1/a_1=-w/h$$

so that r is found.

$$\therefore r=(w^2/2h)+(h/2)$$

(d) A central angle $\angle Q_1 R Q_2$ of a sector in which the line segment $Q_1$-$Q_2$ is a chord is found.

$\Delta Q_1 Q_2 W$ and $\Delta Q_1 R Q_3$ are similar to each other, so that if central angle $\angle Q_1 R Q_2$ is $\theta$(rad), $\angle Q_2 Q_1 W$ is represented by $\theta/2$.

$$\tan(\theta/2)=h/w$$

so that $\theta$ is found.

$$\therefore \theta=2 \times \tan^{-1}(h/w)$$

(e) An arc $Q_1 Q_2$ is found.

If the length of the arc $Q_1 Q_2$ is L, the length of the arc $Q_1 Q_2$ is found by radius×central angle, so that the length L is represented by $$L=|r| \times \theta.$$

r is y-coordinate of the third quadrant, and therefore needs to take an absolute value.

(f) For a point $Q_2'$ such that the length L of the arc $Q_1 Q_2'$ will be the one interpolation distance to be the actual interpolation point, it is necessary to find a length l of a line segment $Q_1$-$Q_2'$.

This length l is represented by l:b=one interpolation distance: L.

$\therefore$ l=one interpolation distance×b/L

As a result, the next interpolation point $Q_2'$ is represented by the point of a position which has moved in a straight line by the length l from the current point $Q_1$ along the interpolation orbital direction vectors VD1 and VD2.

The shape estimation method based on the interpolation method described above is One example. Various other shape estimation methods are possible, such as where the positions of multiple coils are linked by a spline curve. Any one of the methods may be used.

Next, the position of the insertion portion 20 and the operation of detecting a shape such as a looped shape by the apparatus having the above configuration are described.

Figure 18:
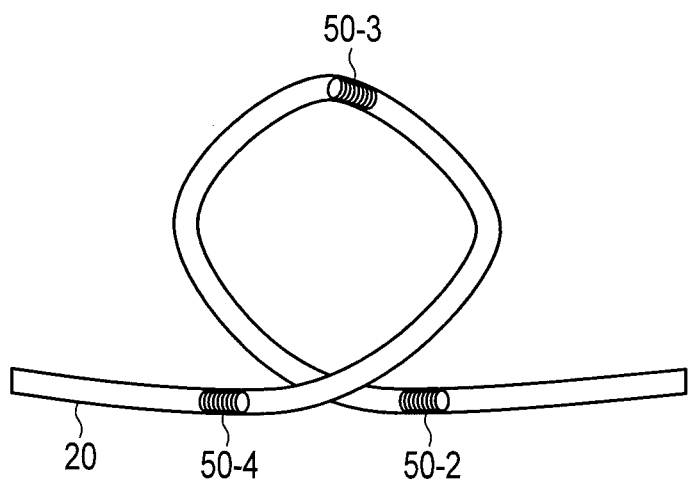
FIG. 18 is a diagram illustrating the detection of the shape of a looped insertion portion according to a background art.

The insertion portion 20 of the endoscope apparatus 10 is inserted into the body cavity of, for example, the patient in accordance with an operation by the operator. The curving portion 23 of the insertion portion 20 curves in, for example, the desired upward, downward, leftward, and rightward (UDLR) directions by the operator's operation. Illumination light is output from the distal end of the insertion portion 20 to illuminate the inside of the body cavity. In this state, an affected part or a lesioned part in the body cavity is observed and treated. When the insertion portion 20 of the endoscope apparatus 10 is inserted into the body cavity in this way, the insertion portion 20 may be looped, for example, as shown in FIG. 18.

First, the signal control unit 56 drives to turn on and off each of the relays of the relay unit 51 in the initial frame period (first), supplies electric power to the transmitting coils 50-1, 50-2, . . . , and 50-$n$ in this order from the transmission electric power supply 52 through the relay unit 51, and sequentially transmits magnetic fields from the transmitting coils 50-1 to 50-$n$ in a time-division manner.

The receiving coils 53-1 to 53-$m$ respectively detect the magnetic fields transmitted from the transmitting coils 50-1 to 50-$n$ in the xyz directions, and generate voltages corresponding to the magnitude of the magnetic fields in the xyz directions at both ends of the receiving coils 53-1 to 53-$m$.

The voltage detector 54 connected to the output terminal of each of the receiving coils 53-1 to 53-$m$ detects each voltage level generated at the output terminal of each of the receiving coils 53-1 to 53-$m$, and outputs each voltage detection signal corresponding to each of the voltage levels. Each of the voltage detection signals is sent to the position detection unit 55.

Each of the voltage detection signals output from the voltage detectors 54 is input to the position detection unit 55. The position detection unit 55 detects each of the coil positions of the transmitting coils 50-1 to 50-$n$ on the basis of the magnitude of each of the voltage levels indicated by each of the voltage detection signals, that is, the magnitude of each of the magnetic fields in the xyz directions, and also detects the direction of each of the receiving coils 53-1 to 53-$m$ from the magnitude of each of the magnetic fields in the xyz directions. The coil positions and coil directions of the transmitting coils 50-1 to 50-$n$ detected by the position detection unit 55 are stored in the memory 19$a$ in the controller 19 as positional information.

After the end of the initial frame period and the end of the transmission of the magnetic fields from the transmitting coils 50-1 to 50-$n$, the shape estimating unit 57 estimates the shape of the insertion portion 20 which is inserted in a body cavity of a subject such as a human body and thus curved, for example, a shape such as a looped shape, on the basis of each of the coil positions of all the transmitting coils 50-1 to 50-$n$ detected by the position detection unit 55 in the initial frame period by the inter-transmission-coil shape estimation method described above in the section [Inter-coil shape estimation method], that is, by sequentially finding pairs of interpolation points from the transmitting coils 50-1 and 50-2 and linking all these interpolation points.

The signal control unit 56 then sequentially controls the even-numbered transmitting coils 50-2, . . . , and 50-$n$ to transmit magnetic fields in a time-division manner in a frame period (second) that is, the even-numbered frame period. That is, the signal control unit 56 drives to turn on each of the relays in the relay unit 51 corresponding to the even-numbered transmitting coils 50-2, . . . , and 50-$n$, sequentially supplies electric power to the even-numbered transmitting coils 50-2, . . . , and 50-$n$ from the transmission electric power supply 52 through the relay unit 51, and sequentially transmits magnetic fields from the transmitting coils 50-1 to 50-$n$ in a time-division manner.

The receiving coils 53-1 to 53-$m$ sequentially detect the magnetic fields respectively transmitted from the even-numbered transmitting coils 50-2, . . . , and 50-$n$ in a time-division manner in the xyz directions, and generate voltages corresponding to the magnitude of the magnetic fields in the xyz directions at both ends of the receiving coils 53-1 to 53-$m$. Thus, as described above, the position detection unit 55 detects each of the coil positions of the even-numbered transmitting coils 50-2, . . . , and 50-$n$. Each of the coil positions of the even-numbered transmitting coils 50-2, . . . , and 50-$n$ is stored in, for example, the memory 19$a$ in the controller 19.

The shape estimating unit 57 reads each of the coil positions of the even-numbered transmitting coils 50-2, . . . , and 50-$n$ detected by the position detection unit 55 from the memory 19$a$ in the frame period (second).

The shape estimating unit 57 reads, from the memory 19$a$, each of the coil positions of the odd-numbered transmitting coils 50-1, . . . , and 50-$n$−1 among all the transmitting coils 50-1 to 50-$n$ already detected from the memory 19$a$ by the position detection unit 55 in a frame period closest to the second frame period, that is, the previous first frame period.

The shape estimating unit 57 estimates the shape, for example, looped shape of the insertion portion 20 by linking the coil positions of the transmitting coils 50-1 to 50-$n$ in accordance with the inter-coil shape estimation method described above in the section [Inter-coil shape estimation method], on the basis of each of the coil positions of the odd-numbered transmitting coils 50-1, . . . , and 50-$n$−1 detected by the position detection unit 55, and the coil positions and coil directions of the even-numbered transmitting coils 50-2, . . . , and 50-$n$ read from the memory 19$a$.

The signal control unit 56 then sequentially controls the odd-numbered transmitting coils 50-1, . . . , and 50-$n$−1 to transmit magnetic fields from in a time-division manner in a third frame period, that is, the odd-numbered frame period.

The receiving coils 53-1 to 53-$m$ sequentially detect the magnetic fields respectively transmitted from the odd-numbered transmitting coils 50-1, . . . , and 50-$n$−1 in a time-division manner in the xyz directions, and generate voltages corresponding to the magnitude of the magnetic fields in the xyz directions at both ends of the receiving coils 53-1 to 53-$m$. Thus, as described above, the position detection unit 55 detects each of the coil positions of the odd-numbered transmitting coils 50-1, . . . , and 50-$n$−1. Each of the coil positions of the odd-numbered transmitting coils 50-1, . . . , and 50-$n$−1 is stored in, for example, the memory 19$a$ in the controller 19.

As described above, the shape estimating unit 57 estimates the shape, for example, looped shape of the insertion portion 20 by interpolating and linking the coils in accordance with the inter-coil shape estimation method described above in the section [Inter-coil shape estimation method], on the basis of each of the coil positions of the odd-numbered transmitting coils 50-1, . . . , and 50-$n$−1 detected by the position detection unit 55 when the magnetic fields are sequentially transmitted from the odd-numbered transmitting coils 50-1, . . . , and 50-$n$−1 in a time-division manner, and each of the coil positions of the even-numbered transmitting coils 50-2, . . . , and 50-$n$ already detected by the position detection unit 55 and stored in the memory 19$a$ in a frame period closest to this third frame period, for example, in the previous second frame period.

Subsequently, in the even-numbered frame period, the shape, for example, looped shape of the insertion portion 20 is estimated by interpolating and linking the coils in accordance with the inter-coil shape estimation method described above in the section [Inter-coil shape estimation method], on the basis of each of the coil positions of the even-numbered transmitting coils 50-2, . . . , and 50-$n$ detected when the magnetic fields are sequentially transmitted from the even-numbered transmitting coils 50-2, . . . , and 50-$n$ in a time-division manner, and each of the coil positions of the odd-numbered transmitting coils 50-1, . . . , and 50-$n$−1 already detected in a frame period closest to this even-numbered frame period, for example, in the previous frame period.

In the odd-numbered frame period, the shape, for example, looped shape of the insertion portion 20 is estimated by interpolating and linking the coils in accordance with the inter-coil shape estimation method described above in the section [Inter-coil shape estimation method], on the basis of each of the coil positions of the odd-numbered transmitting coils 50-1, . . . , and 50-$n$−1 detected when the magnetic fields are sequentially transmitted from the odd-numbered transmitting coils 50-1, . . . , and 50-$n$−1 in a time-division manner, and each of the coil positions of the even-numbered transmitting coils 50-2, . . . , and 50-$n$ already detected in a frame period closest to this odd-numbered frame period, for example, in the previous frame period.

Thus, according to the first embodiment described above, in the even-numbered frame period, the magnetic fields are sequentially transmitted from the even-numbered transmitting coils 50-2, . . . , and 50-$n$ in a time-division manner, and the shape, for example, looped shape of the insertion portion 20 is estimated on the basis of each of the coil positions of the even-numbered transmitting coils 50-2, . . . , and 50-$n$ and each of the coil positions of the odd-numbered transmitting coils 50-1, . . . , and 50-$n$−1 already detected in the closest frame period. In the odd-numbered frame period, the magnetic fields are sequentially transmitted from the odd-numbered transmitting coils 50-1, . . . , and 50-$n$−1 in a time-division manner, and the shape, for example, looped shape of the insertion portion 20 is estimated by linking the coil positions of the transmitting coils 50-1 to 50-$n$ on the basis of the coil positions of each of the odd-numbered transmitting coils 50-1, . . . , and 50-$n$−1, and the coil positions and directions of each of the even-numbered transmitting coils 50-2, . . . , and 50-*n* already detected in the closest frame period.

For example, as shown in FIG. 4, the position of the insertion portion 20 and a shape such as a looped shape are estimated on the basis of each of the coil positions of the even-numbered transmitting coils 50-2, 50-4, and others and each of the coil positions of the odd-numbered transmitting coils 50-1, 50-3, and others already detected by the position detection unit 55 and stored in the memory 19*a*. Therefore, when magnetic fields are transmitted from the even-numbered transmitting coils 50-2, . . . , and 50-*n*, the shape, for example, looped shape of the insertion portion 20 can be estimated even if the even-numbered transmitting coils 50-2, . . . , and 50-*n* are not detected in the looped shape of the insertion portion 20.

Thus, magnetic fields are not transmitted from all the transmitting coils 50-1 to 50-*n* in a time-division manner in every frame period, and the coil positions of all the transmitting coils 50-1 to 50-*n* are not detected, so that the frame rate does not decrease. For example, the configuration of the present instrument 1 is not greatly changed in comparison with the case in which the magnetic fields are sequentially transmitted from all the transmitting coils 50-1 to 50-*n* in every frame period to estimate the shape of the insertion portion 20. The frame rate to estimate the shape of the insertion portion 20 can be about twice as high. The size of the instrument 1 is not changed. Moreover, the price does not increase either.

When the position of each of the transmitting coils detected by sequentially transmitting magnetic fields from the transmitting coils 50-2, . . . , and 50-*n* and the already detected coil position of each of the transmitting coils are used, this is equivalent to the detection of the coil positions of all the transmitting coils 50-1 to 50-*n*, so that the shape, for example, looped shape of the insertion portion 20 can be certainly estimated even if the insertion portion 20 is looped.

Second Embodiment

Next, a second embodiment of the present invention is described with reference to the drawings.

The configuration of the present instrument 1 in this embodiment is the same, so that the differences are only described using FIGS. 1 and 2 together.

In the initial frame period (first), the signal control unit 56 controls all the transmitting coils 50-1 to 50-*n* to transmit magnetic fields in a time-division manner.

In the first frame period (even-numbered frame) among the frame periods after the initial frame period, the signal control unit 56 sequentially controls the even-numbered transmitting coils 50-2, . . . , and 50-*n* as the predetermined coils among the transmitting coils 50-1 to 50-*n* to transmit magnetic fields.

In the same even-numbered frame period, the shape estimating unit 57 estimates the coil position of each of the odd-numbered transmitting coils 50-1, . . . , and 50-*n*–1 on the basis of the coil position adjacent to each of the odd-numbered transmitting coils 50-1, . . . , and 50-*n*–1. The shape estimating unit 57 estimates the shape, for example, looped shape of the insertion portion 20 by linking the coil positions of the transmitting coils 50-1 to 50-*n* on the basis of the estimated coil positions, the coil position and coil direction of each of the even-numbered transmitting coils 50-2, . . . , and 50-*n* already detected in the closest frame period, and each of the distances between the transmitting coils 50-1 to 50-*n*.

In the frame period of the second frame period (odd-numbered frame), the signal control unit 56 sequentially controls the odd-numbered transmitting coils 50-1, . . . , and 50-*n*–1 as the predetermined coils among the transmitting coils 50-1 to 50-*n* to transmit magnetic fields.

In the same odd-numbered frame period, the shape estimating unit 57 estimates the coil position of each of the even-numbered transmitting coils 50-2, . . . , and 50-*n* on the basis of the coil position adjacent to each of the even-numbered transmitting coils 50-2, . . . , and 50-*n*. The shape estimating unit 57 estimates the shape, for example, looped shape of the insertion portion 20 by linking the coil positions of the transmitting coils 50-1 to 50-*n* on the basis of the estimated coil positions, the coil position and coil direction of each of the odd-numbered transmitting coils 50-1, . . . , and 50-*n*–1 already detected in the closest frame period, and each of the distances between the transmitting coils 50-1 to 50-*n*.

The shape estimating unit 57 estimates the coil position of each of the predetermined coils, that is, the coil position of each of the odd-numbered transmitting coils 50-1, . . . , and 50-*n*–1 and the coil position of each of the even-numbered transmitting coils 50-2, . . . , and 50-*n* on the basis of the positions of the predetermined coils, that is, the coil position of each of the even-numbered transmitting coils 50-2, . . . , and 50-*n* or the coil position of each of the odd-numbered transmitting coils 50-1, . . . , and 50-*n*–1, and one or both of the coil position of each of the transmitting coils provided adjacent to the predetermined coil and the adjacent direction.

Specifically, in the initial frame period, the shape estimating unit 57 estimates the shape, for example, looped shape of the insertion portion 20 by linking the coil positions of the transmitting coils 50-1 to 50-*n* on the basis of the coil position and coil direction of each of the transmitting coils 50-1 to 50-*n* detected by the position detection unit 55 when the magnetic fields are transmitted from the transmitting coils 50-1 to 50-*n*, and each of the distances between the transmitting coils 50-1 to 50-*n*.

In each of the frame periods after the initial frame period, the shape estimating unit 57 estimates the smooth shape of the insertion portion 20 from the coil directions and coil positions of the predetermined coils (the even-numbered transmitting coils 50-2, . . . , and 50-*n* and the odd-numbered transmitting coils 50-1, . . . , and 50-*n*–1) on the basis of each of the voltage detection signals output from the voltage detectors 54, that is, each of the voltage detection signals corresponding to each of the voltage levels generated at the output terminal of each of the receiving coils 53-1 to 53-*m*. The shape estimating unit 57 estimates the coil position of the transmitting coil 50-2 that may actually exist, from the shape of the insertion portion 20, and the coil direction and coil position of the transmitting coil 50-1 in the previous frame period of the transmitting coil other than the predetermined coil (each of the odd-numbered transmitting coils 50-1, . . . , and 50-*n*–1 or each of the even-numbered transmitting coils 50-2, . . . , and 50-*n*).

The shape estimating unit 57 estimates the shape, for example, looped shape of the insertion portion 20 by linking the coil positions of the transmitting coils 50-1 to 50-*n* in accordance with the inter-coil shape estimation method described above in the section [Inter-coil shape estimation method], on the basis of the coil position estimated by use of the predicted position of the coil (existence probability of the coil), each of the coil positions and magnetic field directions of the predetermined coils already detected in the closest frame period, and each of the distances between the transmitting coils 50-1 to 50-*n*.

A specific shape estimation method that uses the predicted position of the coil (existence probability of the coil) is described.

In the first embodiment, for example, the looped shape of the insertion portion 20 can be estimated with a certain degree of accuracy even if the number of the transmitting coils 50-1 to 50-$n$ is small. However, for example, when the movement of the scope including the insertion portion 20 is fast or when the scope tends to move, there is a greater difference in the coil position of each of the transmitting coils 50-1 to 50-$n$ between the recent frame period and the current frame period, and the estimated shape differs from the actual shape. Even in such a case, according to the present second embodiment, the shape, for example, looped shape of the insertion portion 20 can be accurately estimated.

A specific example in which the scope tends to move is shown, and a phenomenon that occurs in the above-described first embodiment in which the estimated shape differs from the actual shape is described, wherein given successive two frames are the first frame and the second frame, respectively, as shown by (1) and (2) below. In the explanation below, both the first frame and the second frame are frames in the frame periods after the initial frame period, and the first frame is an odd-numbered frame, and the second frame is an even-numbered frame.

(1) First Frame

Figure 11:
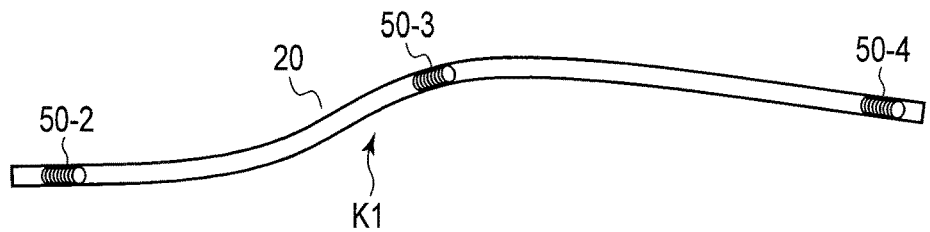
FIG. 11 is a diagram showing the actual shape of the insertion portion and the position of each transmitting coil provided therein in the first frame in the same instrument.

FIG. 11 shows an actual shape K1 of the insertion portion 20 and the coil position of each of the transmitting coils 50-1 to 50-$n$ provided therein in the first frame. FIG. 11 shows each of the transmitting coils 50-2 to 50-4.

In the first frame, the signal control unit 56 sequentially controls the odd-numbered transmitting coils 50-1 to 50-$n$−1 to transmit magnetic fields in a time-division manner.

The shape estimating unit 57 detects the coil position and coil direction of each of the transmitting coils 50-1 to 50-$n$−1 detected by the position detection unit 55 when the magnetic fields are sequentially transmitted from the odd-numbered transmitting coils 50-1 to 50-$n$−1 in a time-division manner in the initial one frame.

(2) Second Frame

FIG. 12 shows an actual shape K2 of an insertion portion 20-1 and the actual coil position of each of the transmitting coils 50-1 to 50-$n$ provided therein in the frame next to the first frame (i.e., the second frame). FIG. 12 shows the shape K1 of the insertion portion 20 in the first frame over the actual shape K2 of the insertion portion 20-1 in the second frame.

The second frame is an even-numbered frame, so that the signal control unit 56 sequentially controls the even-numbered transmitting coils 50-2, . . . , and 50-$n$ among the transmitting coils 50-1 to 50-$n$ to transmit magnetic fields in a time-division manner. Thus, the shape estimating unit 57 estimates the shape of the insertion portion 20-1 in the second frame on the basis of the coil position and coil direction of each of the even-numbered transmitting coils 50-2, . . . , and 50-$n$ detected in the second frame, and the coil position and coil direction of each of the odd-numbered transmitting coils 50-1, . . . , and 50-$n$−1 already detected in the previous initial frame period.

In the state shown in the second frame, the insertion portion 20 is pressed from the side of the operation unit 30 (the right side in the drawing) (press direction M), and the transmitting coil 50-3 close to the operation unit 30 moves to the left side, whereas the transmitting coil 50-1 close to the distal end of the insertion portion 20 does not smoothly move to the left side. Due to this state, in the second frame period, the shape K2 of the insertion portion 20 is curved into, for example, a bow shape, and is different from the shape K1 of the insertion portion 20 in the initial frame period. In such a situation in which the transmitting coil 50-2 tends to move and the difference in the transmitting coil positions between frames is great, the estimated shape of the insertion portion may be different from the actual shape K2 of the insertion portion 20 in the first embodiment.

In the present embodiment, when the difference in the transmitting coil positions between frames is great, the shape estimation method that uses the smoothness of the shape and the existence probability of the coil is also employed to reduce the difference between the actual shape K2 of an insertion portion 20 and the estimated shape of the insertion portion 20.

An overview of the shape estimation method that uses the existence probability is described.

In the first embodiment described above, the shape of the insertion portion 20 in the endoscope apparatus 10 may be estimated to be a non-smooth unnatural shape such as the shape K2 shown in FIG. 12.

In contrast, the shape estimation method according to the present embodiment allows a smoother shape of the insertion portion 20, and still sets the position of the transmitting coil 50-3 at the position which is not that far from the coil position of the transmitting coil 50-3 in the closest frame, for example, the previous frame.

Figure 13:
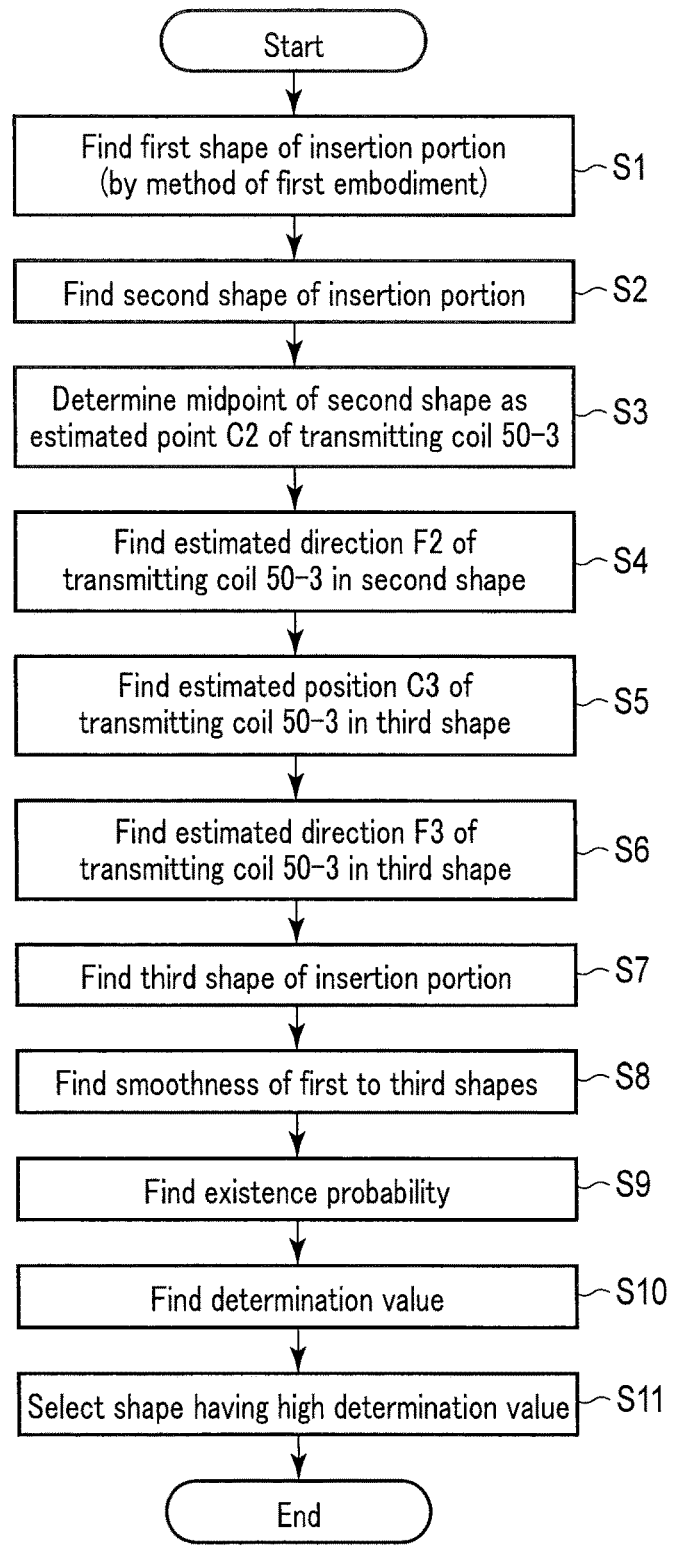
FIG. 13 is a shape estimation flowchart in the same instrument.

The shape estimation method that uses the existence probability as the shape estimation method according to the present embodiment is specifically described below along with a shape estimation flowchart shown in FIG. 13.

Figure 14:
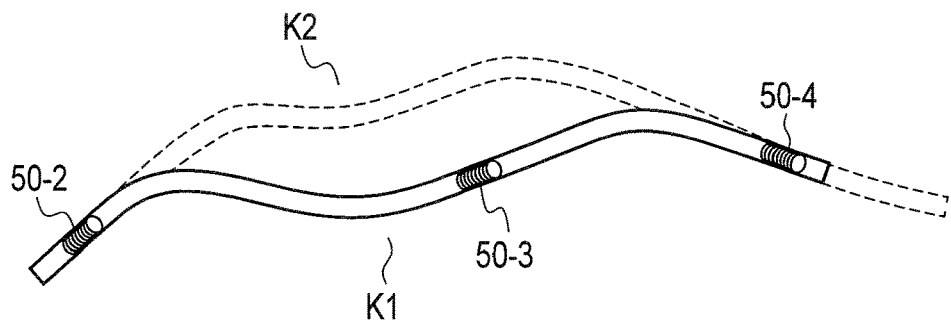
FIG. 14 is a diagram showing the shape of the insertion portion estimated by the estimation method according to the first embodiment in the second frame and the actual shape of the insertion portion during the second frame period in the same instrument.

FIG. 14 shows the coil position of the transmitting coil 50-3 estimated by the estimation method according to the first embodiment in the first frame, and the actual shape K2 of the insertion portion 20 in the second frame.

In step S1, in the second frame, the shape estimating unit 57 estimates, for example, the looped shape of the insertion portion 20 in accordance with the inter-coil shape estimation method described above in the section [Inter-coil shape estimation method], on the basis of the coil position and coil direction of each of the even-numbered transmitting coils 50-2, . . . , and 50-$n$ detected by an estimation method similar to that in the first embodiment, that is, by sequentially transmitting magnetic fields from the even-numbered transmitting coils 50-2, . . . , and 50-$n$ in a time-division manner in the even-numbered frame period, and the coil position and coil direction of each of the odd-numbered transmitting coils 50-1, . . . , and 50-$n$−1 already detected in the recent frame (previous frame).

Figure 15:
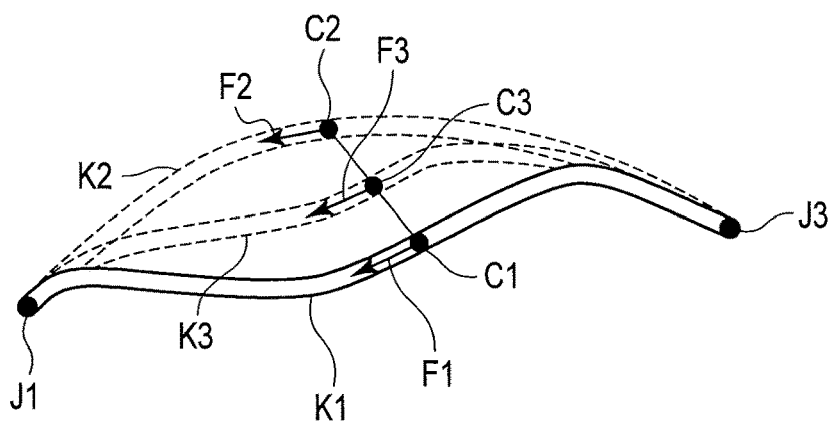
FIG. 15 is a diagram showing first to third shapes of the insertion portion estimated by a shape estimating unit in the same instrument.

In step S2, the shape estimating unit 57 estimates the shape of the part between the transmitting coil 50-2 (a coil position J1) and the transmitting coil 50-4 (a coil position J3) by the inter-coil shape estimation method described above in the section [Inter-coil shape estimation method], using the coil position J1 and coil direction of the transmitting coil 50-2 detected in the second frame shown in FIG. 15, the coil position J3 and coil direction of the transmitting coil 50-4 detected in the second frame, and the distance between the transmitting coils (e.g., 200 mm). The distance between the transmitting coils (e.g., 200 mm) corresponds to the distance between the transmitting coil 50-2 and the transmitting coil 50-4 that is the distance of two coils.

FIG. 15 shows the shape of the insertion portion 20 estimated by the shape estimating unit 57. The shape of the insertion portion 20 estimated by step S1 is represented as K1, and the shape of the insertion portion 20 estimated by step S2 is represented as K2.

In step S3, the shape estimating unit 57 determines a point located at half of the length of the insertion portion 20 along the second shape K2 (when the transmitting coils 50-2, 50-3, and 50-4 are arranged at equal intervals) as an estimated point C2 of the transmitting coil 50-3.

In step S4, the shape estimating unit 57 determines a direction along the shape K2 at the estimated point C2 of the transmitting coil 50-3 as an estimated direction F2 of the transmitting coil 50-3.

In step S5, the shape estimating unit 57 determines a midpoint between the estimated point C2 of the transmitting coil 50-3 and the coil position C1 of the transmitting coil 50-3 in the recent frame (first frame) as an estimated point C3 of the transmitting coil 50-3.

Similarly, in step S6, the shape estimating unit 57 determines the average of the estimated direction F2 of the transmitting coil 50-3 and a direction F1 of the transmitting coil 50-3 in the recent frame (first frame) as an estimated direction F3 of the transmitting coil 50-3 at the estimated point C3.

In step S7, the shape estimating unit 57 finds a third shape K3 of the insertion portion 20 by the inter-coil shape estimation method described above in the section [Inter-coil shape estimation method], using the estimated point C3 of the transmitting coil 50-3 and the estimated direction F3 of the transmitting coil 50-3, the coil position K1 and the coil direction of the transmitting coil 50-2 detected in the second frame, the coil position J3 and the coil direction of the transmitting coil 50-4 detected in the second frame, and the distance between the transmitting coils (e.g., 100 mm). The shape K3 can be said to be an intermediate shape between the shape K1 and the shape K2.

The shape estimating unit 57 may repeat processing similar to that in step S5 to step S7, and find more intermediate shapes, for example, an intermediate shape between the shape K1 and the shape K3 and an intermediate shape between the shape K2 and the shape K3.

Figure 16:
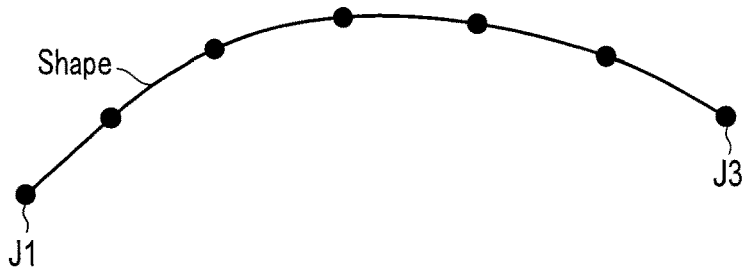
FIG. 16 is a diagram showing the shape between the transmitting coils equally divided by the estimation in the shape estimating unit in the same instrument.

In step S8, the shape estimating unit 57 calculates the smoothness of the first to third shapes K1, K2, and K3 of the insertion portion 20 as follows:

The shape estimating unit 57 divides the shape of the part between the coil position J1 of the transmitting coil 50-2 and the coil position J3 of the transmitting coil 50-4 into N equal parts as shown in FIG. 16. Here, the shape is divided into 6(=N) equal parts.

Figure 17:
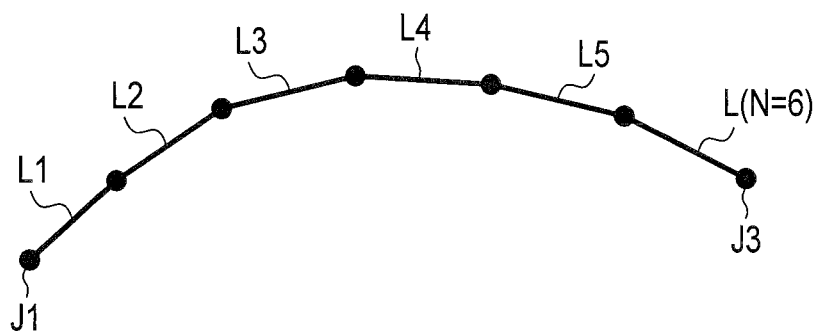
FIG. 17 is a schematic diagram showing each line segment linearized by the shape estimating unit in the same instrument.

The shape estimating unit 57 links the N equal parts by a line, and determines line segments thus obtained as a line L1, a line L2, . . . , and a line LN from the distal end as shown in FIG. 17.

The shape estimating unit 57 calculates angular differences α between the adjacent lines L1, L2, . . . , and LN. In this case, N−1 angular differences α are calculated.

The shape estimating unit 57 determines a reciprocal of the total value of the N−1 angular differences α as the value of smoothness.

In step S9, the shape estimating unit 57 calculates the existence probability of each of the estimated points C1, C2, and C3 of the transmitting coil 50-3 in the first, second, and third shapes K1, K2, and K3 as follows:

The shape estimating unit 57 respectively calculates distances X1, X2, and X3 ($mm$) between the coil position C1 of the transmitting coil 50-3 in the recent frame (first frame) and the estimated points C1, C2, and C3 of the transmitting coil 50-3 in the first to third shapes K1, K2, and K3. The coil position C1 of the transmitting coil 50-3 in the first shape K1 is the coil position of the transmitting coil 50-3 in the recent frame.

The shape estimating unit 57 respectively determines the existence probabilities of the first to third shapes as 100−100·X1/(X1+X2+X3), 100−100·X2/(X1+X2+X3), and 100−100·X3/(X1+X2+X3).

For example, the estimated point C1 of the transmitting coil 50-3 in the first shape K1 is the coil position of the transmitting coil 50-3 in the recent frame, so that the existence probability is 100 when X1=0.

In step S10, the shape estimating unit 57 determines, as a determination value, the value in which the value of smoothness in each shape is added to the value of the existence probability multiplied by k. k is a coefficient representing the difficulty in the change of the position of the scope between frames, and varies depending on the type of scope, the frame rate, and the part in the body in which the scope is located.

In step S11, the shape estimating unit 57 selects and displays a shape having a high determination value from the first to third shapes K1 to K3.

Next, an operation of detecting the position of the insertion portion 20 and a shape such as a looped shape by the apparatus having the above configuration is described.

The insertion portion 20 of the endoscope apparatus 10 is inserted into the body cavity of, for example, the patient by the operator's operation. When the insertion portion 20 is inserted into the body cavity, the insertion portion 20 may be looped, for example, as shown in FIG. 18.

First, in the initial frame period (first), the signal control unit 56 sequentially controls all the transmitting coils 50-1 to 50-$n$ to transmit magnetic fields in a time-division manner.

In the initial frame period, the shape estimating unit 57 estimates the shape, for example, looped shape of the insertion portion 20 inserted in the body cavity of the subject and thus curved on the basis of each of the coil positions of all the transmitting coils 50-1 to 50-$n$ detected by the position detection unit 55.

In the first frame (odd-numbered frame) among the frame periods after the initial frame period, the signal control unit 56 then sequentially controls the odd-numbered transmitting coils 50-1, . . . , and 50-$n$−1 as the predetermined coils among the transmitting coils 50-1 to 50-$n$ to transmit magnetic fields.

The shape estimating unit 57 then detects the positions and directions of the predetermined coils, that is, the odd-numbered transmitting coils 50-1, . . . , and 50-$n$−1 on the basis of each of the voltage detection signals corresponding to each of the voltage levels generated at the output terminal of each of the receiving coils 53-1 to 53-$m$. The shape estimating unit 57 estimates the smooth shape of the insertion portion 20 from the position and direction of each of the odd-numbered transmitting coils among the odd-numbered transmitting coils (step S2).

In this instance, when the even-numbered transmitting coils 50-2, . . . , and 50-$n$ alone exist in the loop as shown in FIG. 18, it is not known by the odd-numbered transmitting coils 50-1, . . . , and 50-$n$−1 alone which direction the looped shape is in, so that one second shape K2 is not determined in contrast to the above, and there are countless second shapes K2.

In this case, the shape estimating unit 57 carries on the processing in and after step S3 in accordance with representative i second shapes K2 (K2-1, K2-2, . . . , and K2-$i$), and finds i×2+1 candidate shapes from the position and direction of each of the transmitting coils 50-2, . . . , and 50-$n$ already detected by the position detection unit 55 in the previous frame. The shape estimating unit 57 selects the shape of the part between the odd-numbered transmitting coils 50-1, ..., and **50-*n*–1** from the candidate shapes in accordance with the smoothness of the shapes and the existence probability.

Thus, the shape estimating unit 57 estimates the shape of the whole insertion portion 20 by selecting the shapes of the parts between the odd-numbered transmitting coils 50-1, ..., and **50-*n*–1**.

On the other hand, in the second (even-numbered frame) frame period among the frame periods after the initial frame period, the signal control unit 56 sequentially controls the even-numbered transmitting coils 50-2, ..., and **50-*n* as the predetermined coils among the transmitting coils 50-1 to 50-*n*** to transmit magnetic fields.

As in the odd-numbered frame, the shape estimating unit 57 then detects the positions and directions of the predetermined coils, that is, the even-numbered transmitting coils 50-2, ..., and **50-*n* on the basis of each of the voltage detection signals corresponding to each of the voltage levels generated at the output terminal of each of the receiving coils 53-1 to 53-*m*. The shape estimating unit 57 estimates the smooth shape of the insertion portion 20 from the position and direction of each of the even-numbered transmitting coils 50-2, ..., and 50-*n* among the even-numbered transmitting coils 50-2, ..., and 50-*n***.

The shape estimating unit 57 then finds candidate shapes from the position and direction of each of the odd-numbered transmitting coils 50-1, ..., and **50-*n*–1 already detected by the position detection unit 55 in the previous frame. The shape estimating unit 57 selects the shapes of the parts between the even-numbered transmitting coils 50-2, ..., and 50-*n*** from the candidate shapes in accordance with the smoothness of the shapes and the existence probability.

Thus, the shape estimating unit 57 estimates the shape of the whole insertion portion 20 by selecting the shapes of the parts between the even-numbered transmitting coils 50-2, ..., and **50-*n***.

Thus, according to the second embodiment described above, the coil positions and coil directions of the predetermined coils (the even-numbered transmitting coils 50-2, ..., and **50-*n* or the odd-numbered transmitting coils 50-1, ..., and 50-*n*–1) are detected, and the existence probability of the predetermined coils already detected in the recent frame existing around each coil position is set, and then the shape, for example, looped shape of the insertion portion 20 is estimated using this existence probability and the smoothness of the shapes. Therefore, in the second embodiment described above, advantageous effects similar to those in the previously described first embodiment are provided, and the shape, for example, looped shape of the insertion portion 20 can be more accurately estimated, for example, even when the movement of the scope including the insertion portion 20** is fast or when the scope tends to move.

As another embodiment, when some of the transmitting coils 50-1 to **50-*n* are determined to be continuously out of magnetic field detection ranges of the receiving coils 53-1 to 53-*m* in a predetermined period, for example, in a period of several frames or more, the signal control unit 56 may control these transmitting coils to transmit magnetic fields and directly detect the coil positions of the transmitting coils 50-1 to 50-*n*** in the initial frame period after the period of several frames or more.

Thus, whenever the scope goes out of the magnetic field detection range and then returns to the detection range, magnetic fields are always transmitted and the positions are directly detected. As a result, the shape is not detected on the basis of old coil position information of several frames or more before. It is possible to more accurately estimate the shape even when the scope temporarily goes out of the detection range and then returns to the detection range.

As another embodiment, the signal control unit 56 sequentially controls the odd-numbered transmitting coils 50-1, ..., and **50-*n*–1 as the predetermined coils among the transmitting coils 50-1 to 50-*n*** to transmit magnetic fields in the second frame period (odd-numbered frame period) among the frame periods after the initial frame period.

In the odd-numbered frame period, the shape estimating unit 57 estimates the coil position of each of the even-numbered transmitting coils 50-2, ..., and **50-*n* on the basis of the coil position of each of the odd-numbered transmitting coils 50-1, ..., and 50-*n*–1 adjacent to each of the even-numbered transmitting coils 50-2, ..., and 50-*n*. The shape estimating unit 57 estimates the coil position of each of new even-numbered transmitting coils 50-2, ..., and 50-*n* on the basis of the distance between the coil position of each of the even-numbered transmitting coils 50-2, ..., and 50-*n* already detected by the position detection unit 55 in a frame period closest to the odd-numbered frame period and the estimated coil positions of the odd-numbered transmitting coils 50-1, ..., and 50-*n*–1. The shape estimating unit 57 estimates the shape of the insertion portion 20 on the basis of the newly estimated coil positions of the even-numbered transmitting coils 50-2, ..., and 50-*n* and the coil position of each of the odd-numbered transmitting coils 50-1, ..., and 50-*n*–1**.

The shape estimating unit 57 estimates the coil position and the coil direction of each of the even-numbered transmitting coils 50-2, ..., and **50-*n* on the basis of the coil position and the coil direction of each of the odd-numbered transmitting coils 50-1, ..., and 50-*n*–1 adjacent to each of the even-numbered transmitting coils 50-2, ..., and 50-*n*. The shape estimating unit 57 estimates the shape of the insertion portion 20 on the basis of the coil position and the coil direction that have been estimated and the coil position and the coil direction of each of the odd-numbered transmitting coils 50-1, ..., and 50-*n*–1**.

The shape estimating unit 57 estimates the coil position of each of the new even-numbered transmitting coils 50-2, ..., and **50-*n* on the basis of the smoothness of the shape of the insertion portion 20** as well.

The present invention is not completely limited to the embodiments described above, and modifications of components can be made at the stage of carrying out the invention without departing from the spirit thereof. Further, various inventions can be made by properly combining the components disclosed in the embodiments described above. For example, some of all the components shown in the embodiments may be eliminated. Moreover, the components in different embodiments may be properly combined.

The transmitting coils 50-1 to **50-*n* are provided in, but not exclusively, the insertion portion 20 of the endoscope apparatus 10 in each of the embodiments described above. The receiving coils 53-1 to 53-*m* may be provided in the insertion portion 20 and the transmitting coils may be provided in the antenna 53. In this case, the shape of the insertion portion 20 is estimated on the basis of the position of each of the receiving coils provided in the insertion portion 20. In this instance, the receiving coils which process received signals output from the receiving coils 53-1 to 53-*m* are selected from the receiving coils 53-1 to 53-*m*** in each frame period. Consequently, it is possible to reduce the size of the circuit configuration which processes the received signals without a decrease in frame rate.

Although the coils transmit and receive magnetic fields in the embodiments described above, any material that can transmit and receive magnetic fields is possible. For example, hall elements, MI sensors, or tunnel magnetoresistive (TMR) sensors are also possible.

What is claimed is:

1. A medical instrument comprising:
an insertion portion configured to be inserted into a subject;
first transmitting coils provided in the insertion portion along a longitudinal direction of the insertion portion at predetermined intervals, wherein the first transmitting coils are configured to transmit magnetic fields;
second transmitting coils provided at positions different from positions of the first transmitting coils in the insertion portion along the longitudinal direction of the insertion portion at predetermined intervals, wherein the second transmitting coils are configured to transmit magnetic fields;
an antenna configured to detect the magnetic fields transmitted by the first transmitting coils and the magnetic fields transmitted by the second transmitting coils; and
a processor comprising hardware, wherein the processor is configured to:
control the first transmitting coils to transmit a first set of magnetic fields during a first predetermined period, wherein the first set of magnetic fields is detected by the antenna;
determine positions of the first transmitting coils on the basis of the first set of magnetic fields detected by the antenna;
control a memory to store the positions of the first transmitting coils that were determined on the basis of the first set of magnetic fields;
control the second transmitting coils to transmit a second set of magnetic fields during a second predetermined period different from the first predetermined period, wherein the second set of magnetic fields is detected by the antenna;
determine positions of the second transmitting coils on the basis of the second set of magnetic fields detected by the antenna;
receive, from the memory, the stored positions of the first transmitting coils;
estimate positions of the first transmitting coils for a third predetermined period different from the first predetermined period and the second predetermined period;
set an existence probability for each of the estimated positions of the first transmitting coils on the basis of the stored positions of the first transmitting coils that were received from the memory;
calculate positions of the first transmitting coils on the basis of the existence probability for each of the estimated positions of the first transmitting coils and on the basis of the determined positions of the second transmitting coils; and
estimate a shape of the insertion portion on the basis of the calculated positions of the first transmitting coils.

2. The medical instrument according to claim 1, wherein each of the first transmitting coils and each of the second transmitting coils are adjacent to each other and alternately provided in the insertion portion along the longitudinal direction of the insertion portion.

3. The medical instrument according to claim 1, wherein the antenna has a magnetic field detection range, and wherein the processor is configured to:
determine whether the first transmitting coils or the second transmitting coils are out of the magnetic field detection range during a predetermined duration of time, wherein the first predetermined period and the second predetermined period are after the predetermined duration of time; and
in response to determining that the first transmitting coils or the second transmitting coils are out of the magnetic field detection range during the predetermined duration of time, control the first transmitting coils or the second transmitting coils to transmit the first set of magnetic fields during the first predetermined period or the second set of magnetic fields during the second predetermined period respectively.

4. A medical instrument comprising:
an insertion portion configured to be inserted into a subject;
first transmitting coils provided in the insertion portion along a longitudinal direction of the insertion portion at predetermined intervals, wherein the first transmitting coils are configured to transmit magnetic fields;
second transmitting coils provided at positions different from positions of the first transmitting coils in the insertion portion along the longitudinal direction of the insertion portion at predetermined intervals, wherein the second transmitting coils are configured to transmit magnetic fields;
an antenna configured to detect the magnetic fields transmitted by the first transmitting coils and the magnetic fields transmitted by the second transmitting coils; and
a processor comprising hardware, wherein the processor is configured to:
control the first transmitting coils to transmit a first set of magnetic fields during a first predetermined period, wherein the first set of magnetic fields is detected by the antenna;
determine positions of the first transmitting coils on the basis of the first set of magnetic fields detected by the antenna;
control a memory to store the positions of the first transmitting coils that were determined on the basis of the first set of magnetic fields;
control the second transmitting coils to transmit a second set of magnetic fields during a second predetermined period different from the first predetermined period, wherein the second set of magnetic fields is detected by the antenna;
determine positions of the second transmitting coils on the basis of the second set of magnetic fields detected by the antenna;
receive, from the memory, the stored positions of the first transmitting coils;
estimate positions of the first transmitting coils for a third predetermined period different from the first predetermined period and the second predetermined period;
set an existence probability for each of the estimated positions of the first transmitting coils on the basis of the positions of the first transmitting coils that were received from the memory;
estimate provisional shapes of the insertion portion on the basis of the determined positions of the second transmitting coils;
calculate a smoothness for each of the provisional shapes of the insertion portion respectively; and
estimate the shape of the insertion portion on the basis of the smoothness for each of the provisional shapes of the insertion portion and on the basis of the existence probability for each of the estimated positions of the first transmitting coils.

5. The medical instrument according to claim 4, wherein the processor is configured to:
for each respective provisional shape of the provisional shapes:
equally divide the respective provisional shape into line segments;
extend each of the line segments of the respective provisional shape;
calculate angular differences between the extended line segments of the respective provisional shape;
calculate a reciprocal of a total sum of the angular differences; and
set the calculated reciprocal of the total sum of the angular differences as a smoothness of the respective provisional shape.

\* \* \* \* \*